(12) United States Patent
Bristow

(10) Patent No.: US 9,242,920 B2
(45) Date of Patent: Jan. 26, 2016

(54) INTEGRATED PROCESS FOR MAKING ACETIC ACID

(71) Applicant: BP CHEMICALS LIMITED, Middlesex (GB)

(72) Inventor: Timothy Crispin Bristow, East Yorkshire (GB)

(73) Assignee: BP CHEMICALS LIMITED, Middlesex (GB)

( * ) Notice: Subject to any disclaimer, the term of this patent is extended or adjusted under 35 U.S.C. 154(b) by 0 days.

(21) Appl. No.: 14/652,853

(22) PCT Filed: Dec. 19, 2013

(86) PCT No.: PCT/EP2013/077485
§ 371 (c)(1),
(2) Date: Jun. 17, 2015

(87) PCT Pub. No.: WO2014/096254
PCT Pub. Date: Jun. 26, 2014

(65) Prior Publication Data
US 2015/0336868 A1   Nov. 26, 2015

(30) Foreign Application Priority Data

Dec. 21, 2012 (EP) .................... 12199102

(51) Int. Cl.
*C07C 51/12* (2006.01)
*C07C 29/151* (2006.01)
*C07C 67/37* (2006.01)
*C07C 41/09* (2006.01)
*C07C 41/16* (2006.01)
*C07C 51/09* (2006.01)

(52) U.S. Cl.
CPC ............ *C07C 51/12* (2013.01); *C07C 29/151* (2013.01); *C07C 29/1518* (2013.01); *C07C 41/09* (2013.01); *C07C 41/16* (2013.01); *C07C 51/09* (2013.01); *C07C 67/37* (2013.01)

(58) Field of Classification Search
CPC ........ C07C 67/37; C07C 29/151; C07C 41/16
See application file for complete search history.

(56) References Cited

U.S. PATENT DOCUMENTS

| | | |
|---|---|---|
| 6,521,783 B1 | 2/2003 | Wegman et al. |
| 6,781,014 B1 | 8/2004 | Vidalin et al. |
| 2011/0124927 A1 * | 5/2011 | Stites et al. ........... C07C 29/149 568/907 |

FOREIGN PATENT DOCUMENTS

| | | |
|---|---|---|
| EP | 1 985 362 A1 | 10/2008 |
| EP | 2 292 578 A1 | 3/2011 |
| GB | 1 306 863 A | 2/1973 |
| GB | EP 2292578 A1 * | 3/2011 |
| WO | WO 03/097523 A2 | 11/2003 |

* cited by examiner

*Primary Examiner* — Paul A Zucker
(74) *Attorney, Agent, or Firm* — Nixon & Vanderhye P.C.

(57) ABSTRACT

An integrated process for the production of acetic acid by carbonylating dimethyl ether with synthesis gas to form methyl acetate and unreacted synthesis gas, utilizing the unreacted synthesis gas to produce methanol, dehydrating and hydrolyzing a mixture of methyl acetate and methanol to produce acetic acid and dimethyl ether and recovering acetic acid therefrom.

31 Claims, 11 Drawing Sheets

INTEGRATED PROCESS FOR MAKING ACETIC ACID

This application is the U.S. national phase of International Application No. PCT/EP2013/077485 filed Dec. 19, 2013 which designated the U.S. and claims priority to European Patent Application No. 12199102.0 filed Dec. 21, 2012, the entire contents of each of which are hereby incorporated by reference.

The present invention relates to an integrated process for the production of acetic acid from synthesis gas and dimethyl ether.

Acetic acid is commercially produced by the liquid phase carbonylation of methanol with carbon monoxide in the presence of a Group VIII noble metal catalyst, typically rhodium or iridium and an alkyl iodide co-catalyst.

Conventionally, acetic acid production requires a supply of methanol reactant from external sources. Methanol is produced commercially by the conversion of synthesis gas containing carbon monoxide, hydrogen and optionally carbon dioxide over a suitable catalyst according to the overall reaction:

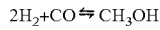

$$2H_2 + CO \rightleftharpoons CH_3OH$$

A major drawback to the parallel production of acetic acid and methanol is that, typically, the carbon monoxide used in acetic acid production processes is substantially pure, as the presence of hydrogen and carbon dioxide therein can be detrimental to acetic acid productivity.

WO 03/097523 describes a process that produces both methanol and acetic acid under substantially stoichiometric conditions, wherein an unadjusted syngas having an R ratio less than 2.0 is provided. All or part of the unadjusted syngas is supplied to a separator unit to recover $CO_2$, CO and hydrogen. At least a portion of any one or combination of the recovered $CO_2$, CO and hydrogen is added to any remaining syngas not so treated or alternatively combined in the absence of any remaining unadjusted syngas to yield an adjusted syngas with a R ratio of 2.0 to 2.9 which is used to produce methanol. Any recovered $CO_2$ not used to adjust the R ratio of the unadjusted syngas can be supplied to the reformer to enhance CO production. At least a portion of the recovered CO is reacted in the acetic acid reactor with at least a portion of the produced methanol to produce acetic acid or an acetic acid precursor by a conventional process.

U.S. Pat. No. 6,781,014 describes a process for the retrofitting of an existing methanol or methanol/ammonia plant to make acetic acid. The existing plant has a reformer to which natural gas or another hydrocarbon and steam are fed. Syngas is formed in the reformer. All or part of the syngas is processed to separate out carbon dioxide, carbon monoxide and hydrogen and the separated carbon dioxide is supplied to the existing methanol synthesis loop for methanol synthesis or back into the feed to the reformer to enhance carbon monoxide formation in the syngas. Any remaining syngas not fed to the carbon dioxide separator can be converted to methanol in the existing methanol synthesis loop along with carbon dioxide from the separator and/or imported carbon dioxide and hydrogen from the separator. The separated carbon monoxide is then reacted with the methanol to produce acetic acid or an acetic acid precursor by a conventional process.

WO 01/07393 describes a process for the catalytic conversion of a feedstock comprising carbon monoxide and hydrogen to produce at least one of an alcohol, ether and mixtures thereof and reacting carbon monoxide with the at least one of an alcohol, ether and mixtures thereof in the presence of a catalyst selected from solid super acids, heteropolyacids, clays, zeolites and molecular sieves, in the absence of a halide promoter, under conditions of temperature and pressure sufficient to produce at least one of an ester, acid, acid anhydride and mixtures thereof GB 1306863 describes a process for producing acetic acid, which comprises the following steps: (a) reacting a gaseous mixture of carbon monoxide and hydrogen in a molar ratio of 1:not more than 0.5, with methanol in the gas phase in the presence of a transition metal catalyst and a halogen-containing compound co-catalyst until no more than half of the carbon monoxide is consumed; (b) cooling the reacted gas obtained in step (a), separating the cooled gas into a liquid component containing acetic acid and a gaseous component containing unreacted carbon monoxide and hydrogen, and withdrawing the acetic acid from the reaction system; (c) washing the gaseous component from step (b) with cold methanol; and (d) reacting the washed gaseous component from step (c) in the presence of a copper-containing catalyst to yield methanol and passing this methanol to step (a).

U.S. Pat. No. 5,840,969 describes a process for the preparation of acetic acid comprising, in a first catalytic step, conversion of a hydrogen and carbon monoxide containing synthesis gas to obtain a liquid process stream comprising methanol and, in a second catalytic step, carbonylation of the process stream with carbon monoxide to produce a product stream being rich in the acetic acid product in the presence of catalytic effective amounts of a metal compound selected from Group VIII of the Periodic Table promoted with a halide compound; withdrawing from the carbonylation step a vent gas stream comprising carbon monoxide and residual amounts of acetic acid and halide compound; separating the vent gas stream into a liquid fraction containing a part of the residual amounts of acetic acid and part of the halide compound, and a gaseous fraction with the carbon monoxide and remaining amounts of acetic acid and halide compound; recycling the liquid fraction to the carbonylation step; subjecting the gaseous fraction to liquid absorption to remove the acetic acid and halide compound in the gaseous fraction, to obtain a carbon monoxide rich recycle stream; and introducing the carbon monoxide rich recycle stream into the synthesis gas conversion step.

Synthesis gas comprises carbon monoxide and hydrogen. Optionally carbon dioxide is included. The synthesis gas ratio or stoichiometric number (SN) of a synthesis gas composition is conventionally calculated as $$SN = (H_2 - CO_2)/(CO + CO_2)$$

wherein $H_2$, CO and $CO_2$ represent the composition of the gas on a molar basis.

Desirably, the optimum stoichiometric number of a synthesis gas for use in methanol production is 2.05. Typically, however, processes for the production of methyl acetate by the carbonylation of dimethyl ether with synthesis gas employ synthesis gas with a stoichiometric excess of carbon monoxide. Thus a major drawback to parallel carbonylation and methanol synthesis processes is that hydrogen:carbon monoxide ratios desirable for methanol synthesis are significantly higher than the desired ratios for carbonylation.

A further drawback of processes for the carbonylation of dimethyl ether is that to prevent recycle components from reaching unacceptable levels in the reactor, a purge gas is removed from the process and typically, such purge gases are disposed of by burning. Purge gas from dimethyl ether carbonylation processes contains carbon monoxide and invariably contains some dimethyl ether and methyl acetate. The removal of these valuable components therefore represents a loss of value and reduces the overall efficiency of the carbonylation process.

A yet further drawback is that the introduction of synthesis gas streams containing methyl acetate to methanol synthesis processes has now been found to result in undesirable side-reactions and/or by-products, such as one or more of ethanol and acetic acid, resulting in a detrimental loss of catalytic performance and/or methanol productivity.

As described above, processes for the carbonylation of dimethyl ether with synthesis gas to produce a carbonylation reaction product typically employ synthesis gas with a stoichiometric excess of carbon monoxide. This results in unconsumed carbon monoxide being withdrawn (together with hydrogen which generally remains unconsumed in the process) from the process as part of the carbonylation reaction product. Typically, to avoid loss of carbon monoxide feedstock from the process, it is recycled with unconsumed hydrogen to the carbonylation reactor. A disadvantage of this recycle is that hydrogen builds-up in the reactor and an undesirable reduction in the carbonylation reaction rate is observed.

Furthermore, processes for the carbonylation of dimethyl ether typically require an external supply of dimethyl ether.

It has now been found that the above-described problems may be overcome or at least mitigated by providing an integrated process for the production of acetic acid from synthesis gas comprising hydrogen and carbon monoxide and dimethyl ether.

Accordingly, the present invention further provides an integrated process for the production of acetic acid which process comprises:
(i) feeding synthesis gas and dimethyl ether into a carbonylation reaction zone and reacting therein the synthesis gas and dimethyl ether in the presence of a carbonylation catalyst to form a gaseous carbonylation reaction product comprising methyl acetate and synthesis gas enriched in hydrogen;
(ii) withdrawing carbonylation reaction product from the carbonylation reaction zone and recovering therefrom a methyl acetate-rich liquid stream and a synthesis gas stream;
(iii) passing at least a portion of the synthesis gas recovered from the carbonylation reaction product to a methanol synthesis zone and contacting it therein with a methanol synthesis catalyst to form a methanol synthesis product comprising methanol and unconverted synthesis gas;
(iv) withdrawing methanol synthesis product from the methanol synthesis zone and recovering therefrom a methanol-rich liquid stream and a synthesis gas stream;
(v) supplying at least a portion of the methyl acetate-rich liquid stream and at least a portion of a methanol-rich liquid stream to a dehydration-hydrolysis reaction zone and contacting therein methanol and methyl acetate with at least one catalyst active for the dehydration of methanol and for the hydrolysis of methyl acetate to form a dehydration-hydrolysis reaction product comprising acetic acid and dimethyl ether;
(vi) recovering from the dehydration-hydrolysis reaction product an acetic acid-rich product stream and a dimethyl ether-rich product stream.

In some or all embodiments of the present invention, at least a portion of synthesis gas recovered from the carbonylation reaction product comprising methyl acetate, is scrubbed in a scrubbing zone, which scrubbing zone comprises one or more scrubbing units, with a source of liquid methanol selected from imported methanol, a methanol-rich stream recovered from the methanol synthesis product and mixtures thereof, to generate a scrubbed synthesis gas depleted in methyl acetate and a liquid methanol stream containing methanol and absorbed methyl acetate (a used methanol stream).

In some or all embodiments of the present invention, the methanol-rich stream supplied to the dehydration-hydrolysis reaction zone may be selected from the methanol-rich stream recovered from the methanol synthesis product and a used methanol stream from the scrubbing zone or a mixture of both.

In some or all embodiments of the present invention, the methanol-rich stream supplied to the dehydration-hydrolysis reaction zone is that recovered from the methanol synthesis product.

In some or all embodiments of the present invention, the synthesis feed to the carbonylation reaction zone comprises fresh synthesis gas, which fresh synthesis preferably comprises carbon dioxide and synthesis gas recovered from the carbonylation reaction product.

In some or all embodiments of the present invention, there is supplied to the methanol synthesis zone, synthesis gas recovered from the carbonylation product which synthesis gas is scrubbed or unscrubbed synthesis gas and in addition, one or more sources of synthesis gas selected from fresh synthesis gas, synthesis gas recovered from the methanol synthesis product and mixtures thereof.

In some or all embodiments of the present invention, there is supplied to the methanol synthesis zone, one or more of imported carbon dioxide and water.

In some or all embodiments of the present invention, there is supplied to the dehydration-hydrolysis reaction zone, a methanol-rich liquid stream and a methyl acetate-rich liquid stream and in addition one or more streams comprising one or more of water, methyl acetate and methanol, suitably one or more streams comprising water, methanol and methyl acetate.

In some or all embodiments of the present invention in each of the carbonylation reaction zone, the methanol synthesis zone and the dehydration-hydrolysis reaction zone the reaction is carried out as a heterogeneous vapour phase reaction.

In some or all embodiments of the present invention, dimethyl ether supplied to the carbonylation reaction zone is some or all of a dimethyl ether-rich product stream recovered from a dehydration-hydrolysis reaction zone.

Advantageously, the present invention provides a process for the production of acetic acid from synthesis gas whilst minimising loss of carbon monoxide values. Unreacted carbon monoxide and hydrogen present in carbonylation product streams are usefully converted to methanol thereby eliminating the need for any additional source of synthesis gas for methanol synthesis.

Advantageously, the present invention provides a process which allows for the reduction or complete elimination of the need to dispose of a purge gas from the carbonylation of dimethyl ether, thereby reducing the loss of valuable components such as dimethyl ether, carbon monoxide and methyl acetate.

Advantageously, the present invention provides a process which reduces by-product formation during methanol synthesis by the substantial removal of methyl acetate from feeds to methanol synthesis, thereby mitigating an undesirable loss in methanol productivity and/or loss in catalytic performance.

Desirably, the present invention allows methanol to be produced from synthesis gas feeds which have a stoichiometric number which is sub-optimal for methanol production whilst also allowing the production of methyl acetate.

Furthermore, the present invention allows the production of methanol whilst reducing the need for imported carbon dioxide thereby reducing methanol process costs.

Additionally, the consumption of dimethyl ether feedstock in the production of methyl acetate by carbonylation of dimethyl ether is advantageously reduced.

More desirably, the present invention provides for acetic acid to be produced from a single synthesis gas feed with reduced requirements for fresh dimethyl ether feedstock.

The accompanying drawings, which are incorporated in and constitute part of the specification, illustrate embodiments of the invention and, together with the description, serve to explain the features, advantages, and principles of the invention. In the drawings.

Figure 1:
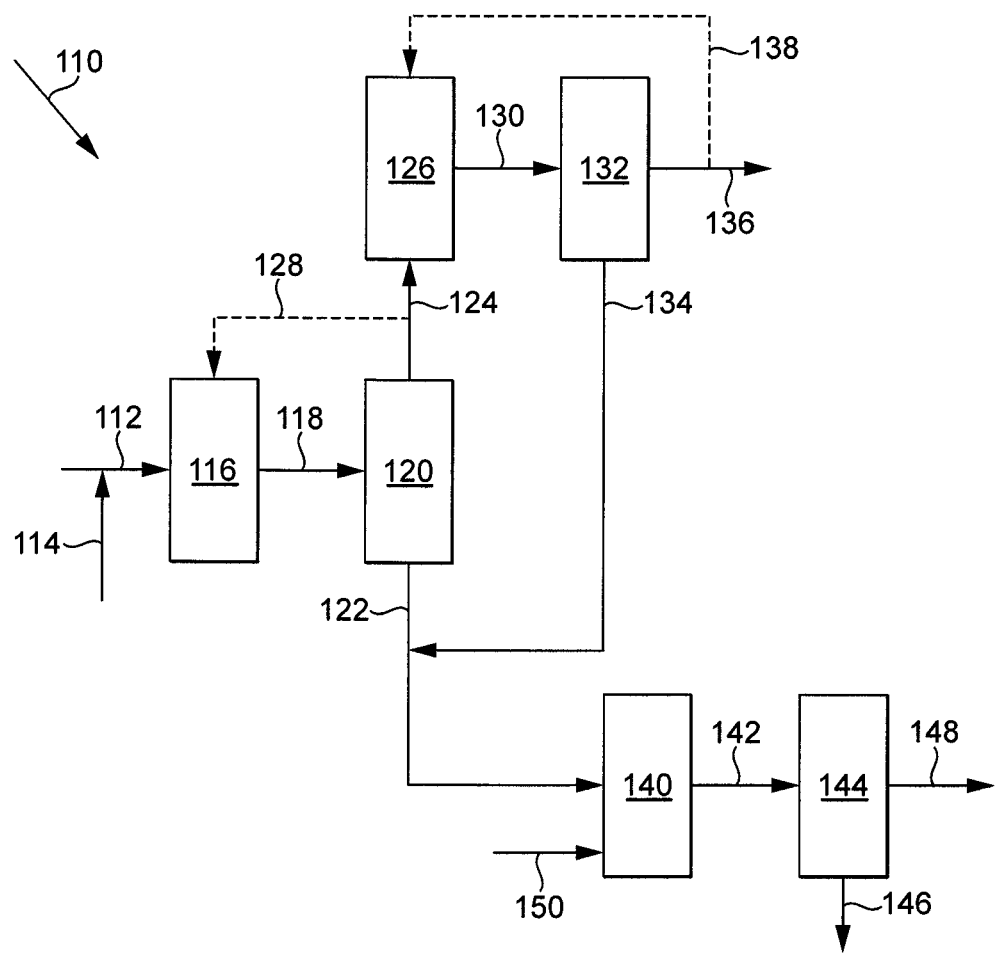
FIG. 1 is a block diagram showing one embodiment of the present invention of an integrated process for the production of acetic acid.

As discussed above, synthesis gas comprises carbon monoxide and hydrogen. Optionally, synthesis gas may also comprise carbon dioxide. Typically, synthesis gas may also comprise small amounts of inert gases such nitrogen and methane. Conventional processes for converting hydrocarbon sources to synthesis gas include steam reforming and partial oxidation. Examples of hydrocarbon sources used in synthesis gas production include bio-mass, natural gas, methane, $C_2$-$C_5$ hydrocarbons, naphtha, coal and heavy petroleum oils.

Steam reforming generally comprises contacting a hydrocarbon with steam to form synthesis gas. The process preferably includes the use of a catalyst, such as those based on nickel.

Partial oxidation generally comprises contacting a hydrocarbon with oxygen or an oxygen-containing gas such as air to form synthesis gas. Partial oxidation takes place with or without the use of a catalyst, such as those based on rhodium, platinum or palladium.

In the present invention, synthesis gas comprising carbon monoxide and hydrogen is contacted with dimethyl ether in a carbonylation reaction zone with a suitable carbonylation catalyst to produce a gaseous carbonylation reaction product comprising methyl acetate and a synthesis gas enriched in hydrogen.

Suitably, the synthesis gas feed to the carbonylation reaction zone is synthesis gas generated by the steam reforming of hydrocarbons or by the partial oxidation of hydrocarbons. Preferably the synthesis gas is generated by the partial oxidation of natural gas or methane.

Suitably, the synthesis gas formed in the synthesis gas generating process is cooled prior to use in the carbonylation reaction. Preferably, the synthesis gas is cooled so as to condense at least a portion of the water vapour formed during the synthesis gas forming process.

Synthesis gas supplied to the carbonylation reaction zone is preferably a dry synthesis gas. Water may be removed from synthesis gas, using any suitable means, for example a molecular sieve.

The synthesis gas feed to the carbonylation reaction zone comprises fresh synthesis gas. For the present purposes, fresh synthesis gas includes freshly produced synthesis gas and also stored sources of synthesis gas. The synthesis gas feed to the carbonylation reaction zone may consist essentially of fresh synthesis gas that is in the absence of any recycle synthesis gas.

Suitably, a fresh synthesis gas feed to the carbonylation reaction zone comprises carbon dioxide. Carbon dioxide may be present in the synthesis gas feed in an amount of not greater than 50 mol %, such as in the range 0.5 to 12 mol %.

The stoichiometric number (SN) of a fresh synthesis gas feed to the carbonylation reaction zone is not critical and may vary significantly. Advantageously, in an embodiment of the present invention, methanol may be produced in the methanol synthesis zone without the need to supply a fresh synthesis gas feed to the methanol synthesis zone in addition to that fed to the carbonylation reaction zone. Preferably, to provide a suitable synthesis gas composition to the methanol synthesis zone for the stoichiometrically balanced production of methanol, a fresh synthesis gas to the carbonylation reaction zone contains at least a partial excess of hydrogen compared to the amount of carbon monoxide and carbon dioxide. Suitably therefore, a fresh synthesis gas has a stoichiometric number in the range 0.9 to 1.3, preferably in the range 1.0 to 1.2, such as in the range 1.0 to 1.1.

However, if desired, fresh synthesis gas may also be supplied to the methanol synthesis zone. Suitably, in this instance, the fresh synthesis gas feed to the methanol synthesis zone is of a composition such that a combined fresh synthesis gas feed to the methanol synthesis zone and a synthesis gas recovered from the carbonylation reaction product has a stoichiometric number which is higher than the stoichiometric number of the synthesis gas feed to the carbonylation reaction zone. Preferably, the synthesis gas feed to the carbonylation reaction zone has a stoichiometric number of 1.1 or less, preferably in the range 0.05 to 1.1. Preferably, a combined fresh synthesis gas to the methanol synthesis zone and synthesis gas recovered from the carbonylation reaction product has a stoichiometric number in the range 1.5 to 2.5, such as in the range 2.0 to 2.1, for example 2.05.

Preferably, the synthesis gas feed to the carbonylation reaction zone further comprises recycle synthesis gas. Suitable sources of recycle synthesis gas include synthesis gas recovered from the carbonylation reaction product.

Preferably, in the present invention, the synthesis gas feed to the carbonylation reaction zone comprises a mixture of fresh synthesis gas and synthesis gas recovered from the carbonylation reaction product.

Recycle synthesis gas, such as that recovered from the carbonylation reaction product, may also comprise carbon dioxide. Preferably, a synthesis gas feed comprising fresh and recycle synthesis gas may comprise carbon dioxide in a total amount of not greater than 50 mol %, such as in the range 0.5 to 12 mol %.

Synthesis gas may be fed to the carbonylation reaction zone as one or more streams. The one or more streams may be either fresh synthesis gas or a mixture of fresh and recycle synthesis gas.

Preferably, prior to use in the carbonylation reaction, the synthesis gas (fresh, recycle and mixtures thereof) is heated, for example in one or more heat exchangers, to the desired carbonylation reaction temperature.

The carbon monoxide partial pressure in the carbonylation reaction zone should be sufficient to permit the production of methyl acetate. Thus, suitably, the carbon monoxide partial pressure is in the range 0.1 to 100 barg (10 kPa to 10,000 kPa), such as 10 to 65 barg (1000 kPa to 6500 kPa).

The hydrogen partial pressure in the carbonylation reaction zone is suitably in the range 1 barg to 100 barg (100 kPa to 10,000 kPa), preferably 10 to 75 barg (1000 kPa to 7500 kPa).

The dimethyl ether feed to the carbonylation reaction zone may be fresh dimethyl ether, recycle dimethyl ether or a mixture of fresh and recycle dimethyl ether. Suitably, recycle streams comprising dimethyl ether may be obtained from any part of the process downstream of the carbonylation reaction zone including, for example synthesis gas streams recovered from the carbonylation reaction product and a dimethyl ether-rich product stream recovered from the dehydration-hydrolysis reaction product.

Suitably, the dimethyl ether feed to the carbonylation reaction zone comprises fresh dimethyl ether and at least a portion, preferably substantially all, of a dimethyl ether-rich product stream recovered from the dehydration-hydrolysis reaction product.

Dimethyl ether may be fed to the carbonylation reaction zone as one or more fresh dimethyl ether streams, one or more recycle streams or as one or more streams comprising a mixture of fresh and recycle dimethyl ether.

Dimethyl ether and synthesis gas may be fed to the carbonylation reaction zone as one or more separate streams, but preferably are supplied as one or more combined synthesis gas and dimethyl ether streams.

In an embodiment, dimethyl ether and synthesis gas are fed to the carbonylation reaction zone as a combined stream, which combined stream is heated to the desired carbonylation reaction temperature, for example in one or more heat exchangers, prior to use in the carbonylation reaction.

In commercial practice, dimethyl ether is produced by the catalytic conversion of methanol over methanol dehydration catalysts. This catalytic conversion results in a product which is predominantly dimethyl ether but it may also contain low levels of methanol, water or both. The presence of significant amounts of water in a zeolite catalysed carbonylation of dimethyl ether tends to inhibit the production of methyl acetate product. In addition, water may be generated in the carbonylation reaction via side-reactions. Dimethyl ether for use in the carbonylation reaction of the present invention may contain small amounts of one or more of water and methanol provided that the total amount of methanol and water is not so great as to significantly inhibit the production of methyl acetate. Suitably, the dimethyl ether (including recycles) may contain water and methanol in a total amount in the range 1 ppm to 10 mol %, for example 1 ppm to 2 mol %, such as 1 ppm to 1 mol %, preferably in the range from 1 ppm to 0.5 mol %.

Preferably, the dimethyl ether (fresh and recycle) feed is dried before use in the carbonylation reaction zone.

Dimethyl ether may be fed to the carbonylation reaction zone at a concentration in the range of 1 mol % to 20 mol %, suitably in the range 1.5 mol % to 15 mol %, for instance 5 to 15 mol %, for example 2.5 to 12 mol %, such as in the range 2.5 to 7.5 mol % based on the total of all streams to the carbonylation reaction zone.

The molar ratio of carbon monoxide to dimethyl ether in the carbonylation reaction zone is suitably in the range 1:1 to 99:1, for example 1:1 to 25:1, such as 2:1 to 25:1.

Carbon dioxide reacts with hydrogen to form water and carbon monoxide. This reaction is commonly referred to as the reverse water gas shift reaction. Thus, where it is desired to utilise a synthesis gas feed comprising carbon dioxide, to mitigate the effect of water on the carbonylation reaction, it is preferred that the carbonylation catalyst is not active for the reverse water-gas shift reaction or for the production of methanol. Preferably, the carbonylation catalyst comprises an aluminosilicate zeolite.

Zeolites comprise a system of channels which may be interconnected with other channel systems or cavities such as side-pockets or cages. The channel systems are defined by ring structures which rings may comprise, for example, 8, 10, or 12 members. Information about zeolites, their framework structure types and channel systems is published in the Atlas of Zeolite Framework Types, C. H. Baerlocher, L. B. Mccusker and D. H. Olson, 6th Revised Edition, Elsevier, Amsterdam, 2007 and is also available on the website of the International Zeolite Association at www.iza-online.org.

Suitably, the carbonylation catalyst is an aluminosilicate zeolite which comprises at least one channel which is defined by an 8-member ring. The aperture of the zeolite channel system defined by the 8-membered ring should be of such dimensions that the reactant dimethyl ether and carbon monoxide molecules can diffuse freely in and out of the zeolite framework. Suitably, the aperture of the 8-member ring channel of the zeolite has dimensions of at least 2.5×3.6 Angstroms. Preferably, the channel defined by the 8-member ring is interconnected with at least one channel defined by a ring with 10 or 12 members.

Non-limiting examples of aluminosilicate zeolites which comprise at least one channel which is defined by an 8-membered ring include zeolites of framework structure type MOR (for example, mordenite), FER (for example, ferrierite), OFF (for example, offretite) and GME (for example, gmelinite).

A preferred carbonylation catalyst is a mordenite zeolite.

The carbonylation catalyst may be a zeolite in its hydrogen form. Preferably, the carbonylation catalyst is mordenite in its hydrogen form.

The carbonylation catalyst may be a zeolite which is fully or partially loaded with one or more metals. Suitable metals for loading onto the zeolite include copper, silver, nickel, iridium, rhodium, platinum, palladium or cobalt and combinations thereof, preferably copper, silver and combinations thereof. Mordenite zeolites containing copper and/or silver and loaded with 0.05 to 10 mol % platinum relative to aluminium are described in European patent application, EP-A-1985362.

The metal loaded form may be prepared by techniques such as ion-exchange and impregnation. These techniques are well-known and typically involve exchanging the hydrogen or hydrogen precursor cations (such as ammonium cations) of a zeolite with metal cations.

The carbonylation catalyst may be an aluminosilicate zeolite which, in addition to aluminium and silicon, has present in its framework one or more additional metals such as trivalent metals selected from at least one of gallium, boron and iron. Suitably, the carbonylation catalyst may be a zeolite which contains gallium as a framework element. More suitably, the carbonylation catalyst is a mordenite which contains gallium as a framework element, most suitably the carbonylation catalyst is a mordenite which contains gallium as a framework element and is in its hydrogen form.

The carbonylation catalyst may be a zeolite which is composited with at least one binder material. As will be appreciated by those of ordinary skilled in the art, binder materials are selected such that the catalyst is suitably active and robust under the carbonylation reaction conditions. Examples of suitable binder materials include inorganic oxides, such as silicas, aluminas, alumina-silicates, magnesium silicates, magnesium aluminium silicates, titanias and zirconias. Preferred binder materials include aluminas, alumina-silicates and silicas, for example, boehemite type alumina.

The relative proportions of the zeolite and the binder material may vary widely but suitably, the binder material may be present in a composite in an amount in the range of 10% to 90% by weight of the composite, preferably, in the range of 10% to 65% by weight of the composite.

Zeolite powders may also be formed into particles without the use of a binder. Typical zeolite catalyst particles include extrudates whose cross sections are circular or embrace a plurality of arcuate lobes extending outwardly from the central portion of the catalyst particles.

In an embodiment of the present invention, the carbonylation catalyst is a zeolite, such as a mordenite, which is composited with at least one inorganic oxide binder material, which may suitably be selected from aluminas, silicas and alumina-silicates, and is utilised in the form of a shaped body, such as an extrudate. In particular, the carbonylation catalyst is a mordenite composited with an alumina, such as a boehmite alumina. The mordenite composited with the alumina may contain gallium as a framework element.

The silica to alumina molar ratio of the zeolites for use as carbonylation catalysts in the present invention is the bulk or overall ratio. This can be determined by any one of a number of chemical analysis techniques. Such techniques include x-ray fluorescence, atomic absorption and ICP (inductive coupled plasma). All will provide substantially the same silica to alumina molar ratio value.

The bulk silica to alumina molar ratio (herein also termed "SAR") of synthetic zeolites will vary. For example, the SAR of a zeolite, such as mordenite, may range from as low as 5 to over 90.

The SAR of a zeolite for use as a carbonylation catalyst in the present invention may suitably be in the range from 10:1 to 90:1, for example 20:1 to 60:1.

It is preferred that a zeolite carbonylation catalyst is activated immediately before use, typically by heating it at elevated temperature for at least one hour under flowing nitrogen, carbon monoxide, hydrogen or mixtures thereof.

Preferably, the carbonylation reaction is carried out under substantially anhydrous conditions. Suitably therefore, as discussed above, to limit the presence of water in the carbonylation reaction, all reactants, including fresh synthesis gas, fresh dimethyl ether, any recycles thereof and the catalyst are dried prior to use in the carbonylation reaction.

Suitably, the combined amount of water and methanol (a source of water) present in the carbonylation reaction zone is limited to be in the range 1 ppm to 0.5 mol %, preferably in the range 1 ppm to 0.1 mol %, and most preferably in the range 1 ppm to 0.05 mol %. Desirably, the combined amount of water and methanol introduced into the carbonylation reaction zone is not more than 0.5 mol %, for example 0 to 0.5 mol %, such as 1 ppm to 0.5 mol %.

The carbonylation catalyst may be employed in a fixed bed carbonylation reaction zone, for example in the shape of pipes or tubes, where the dimethyl ether and synthesis gas feeds, typically in gaseous form are passed over or through the carbonylation catalyst.

The carbonylation reaction is carried out in the vapour phase. Thus, any and all feeds to the carbonylation reaction zone including dimethyl ether are in the vapour phase prior to supply to the carbonylation reaction zone.

Synthesis gas and dimethyl ether are reacted in the presence of the carbonylation catalyst under reaction conditions effective to form a gaseous carbonylation reaction product comprising methyl acetate.

Preferably, the carbonylation reaction is carried out at a temperature in the range of 100° C. to 350° C., for example in the range 250° C. to 350° C.

Preferably, the carbonylation reaction is carried out at a total pressure in the range 1 to 200 barg (100 kPa to 20,000 kPa), for example 10 to 100 barg (1000 kPa to 10,000 kPa), such as 50 to 100 barg (5000 kPa to 10,000 kPa).

In an embodiment, the carbonylation reaction is carried out at temperatures in the range 250° C. to 350° C. and at a total pressure in the range 50 to 100 barg (5000 kPa to 10,000 kPa).

In a preferred embodiment, synthesis gas and dimethyl ether, preferably containing water and methanol in no more than a combined amount in the range 1 ppm to 10 mol %, are reacted in the presence of a carbonylation catalyst, such as an aluminosilicate zeolite having at least one channel which is defined by an 8-membered ring, for example mordenite, preferably mordenite in its hydrogen form, at a temperature in the range 100° C. to 350° C. and at a total pressure in the range 10 to 100 barg (1000 kPa to 10,000 kPa) to form a gaseous carbonylation reaction product comprising methyl acetate and synthesis gas enriched in hydrogen.

Suitably, dimethyl ether and fresh synthesis gas (optionally comprising carbon dioxide, recycle synthesis gas or both) may be fed to the carbonylation reaction zone at a total gas hourly space velocity of flow of gas through the catalyst bed (GHSV) is in the range 500 to 40,000 $h^{-1}$, such as 2000 to 20,000 $h^{-1}$.

Preferably, the carbonylation reaction is carried out substantially in the absence of halides, such as iodide. By the term 'substantially' is meant that the halide, for example the total iodide, content of the feed streams to the carbonylation reaction zone is less than 500 ppm, preferably less than 100 ppm.

Hydrogen present in synthesis gas is essentially inactive in the carbonylation reaction and thus the hydrogen content of synthesis gas withdrawn from the carbonylation reaction zone is enriched relative to the hydrogen content of the synthesis gas feed to the carbonylation reaction zone.

The carbonylation reaction product withdrawn from the carbonylation reaction zone comprises methyl acetate and synthesis gas enriched in hydrogen. Additional components which typically may be present in the carbonylation reaction product include one or more of unreacted dimethyl ether, and small amounts of water, acetic acid and methanol.

Carbon dioxide is generally unconsumed in the carbonylation reaction, thus when the synthesis gas feed to the carbonylation reaction zone comprises carbon dioxide, the carbonylation reaction product will also comprise carbon dioxide.

The carbonylation reaction product is withdrawn from the carbonylation reaction zone in gaseous form.

A methyl acetate-rich liquid stream and a synthesis gas stream are recovered from the carbonylation reaction product.

Suitably, the carbonylation reaction product is withdrawn from the carbonylation reaction zone, cooled and separated to recover a methyl acetate-rich liquid stream and a synthesis gas stream.

Cooling of the carbonylation reaction product may be carried out using any suitable cooling means, for example one or more conventional heat exchangers. The carbonylation reaction product may be cooled to any suitable temperature which allows the recovery of liquid methyl acetate and gaseous synthesis gas. Suitably, the carbonylation reaction product may be cooled to a temperature in the range of 50° C. or less, such as to a temperature in the range 40° C. to 50° C. The cooled carbonylation reaction product may be separated, for example in one or more gas/liquid separation means, such as a knock-out drum or a tangential inlet drum, to recover a methyl acetate-rich liquid stream and a synthesis gas stream. The methyl acetate-rich liquid stream will comprise mainly methyl acetate and may also comprise additional components selected from one or more of unreacted dimethyl ether, methanol, water, acetic acid and dissolved synthesis gas.

Methyl acetate may be recovered from a portion of the methyl acetate-rich liquid stream, for example by distillation, and sold as such or used as a feedstock in downstream chemical processes.

Synthesis gas recovered from the carbonylation reaction product may comprise small amounts of additional components, typically one or more of unreacted dimethyl ether, carbon dioxide, methyl acetate and acetic acid. The recovered synthesis gas may be passed in its entirety to the methanol synthesis zone.

The amount of methyl acetate present in the recovered synthesis gas can vary but it may be present in an amount in the range 0.1 to 5 mol %, for example 0.5 to 5 mol %, such as 0.5 to 2 mol %, for instance 0.5 to 1 mol %. It has now been found that the presence of methyl acetate in synthesis gas feeds to methanol synthesis is highly undesirable as its presence can lead to the formation of unwanted by-products, such as one or more of ethanol and acetic acid, resulting in a loss of performance of the methanol synthesis catalyst, a reduction in methanol productivity or both.

Thus, suitably, where synthesis gas recovered from the carbonylation reaction product comprises methyl acetate the synthesis gas may be subjected to one or multiple scrubbing treatments, such as two or more scrubbing treatments, wherein at least a portion of the synthesis gas is scrubbed in a scrubbing zone comprising one or more scrubbing units with a liquid scrubbing solvent to reduce its methyl acetate content and to obtain a scrubbed synthesis gas depleted in methyl acetate and one or more liquid solvent streams comprising absorbed methyl acetate.

Scrubbing of the synthesis gas to reduce the methyl acetate content thereof is conducted in a scrubbing zone. A scrubbing zone may contain one or more scrubbing units, suitably of conventional design, for example a column or tower within which high surface area materials such as trays or packing, is arranged so as to enable intimate contact of the synthesis gas and the scrubbing solvent and to ensure good mass transfer between the gas and liquid phases. Desirably, scrubbing is performed by counter-current contact of the synthesis gas and the scrubbing solvent such that the synthesis gas flows upwardly through the column or tower and the scrubbing solvent flows downwardly through the column or tower.

Suitably, a liquid stream comprising the scrubbing solvent and methyl acetate is withdrawn from the lower portion of a scrubbing unit.

Suitably, synthesis gas depleted in methyl acetate content is removed from the upper portion of a scrubbing unit.

Synthesis gas recovered from the carbonylation reaction product may be subjected to multiple scrubbing treatments. Each scrubbing treatment may be conducted with the same or different scrubbing solvent.

Where it is desired that synthesis gas is to be subjected to more than one scrubbing treatment, such as two scrubbing treatments, the synthesis gas may be subjected to a first scrubbing treatment by contacting the synthesis gas with a first scrubbing solvent to obtain a liquid solvent stream comprising methyl acetate and synthesis gas depleted in methyl acetate. The synthesis gas depleted in methyl acetate may then be subjected to a second scrubbing treatment by contacting it with a second liquid scrubbing solvent to obtain a liquid solvent stream comprising methyl acetate and synthesis gas further depleted in methyl acetate.

Multiple scrubbing of synthesis gas may and generally does result in the liquid solvent streams obtained from each scrubbing being of a different composition. For example, where a synthesis gas is scrubbed using a scrubbing solvent which is methanol or comprises methanol most of the methyl acetate present in the synthesis gas will be absorbed by the methanol scrubbing solvent in a first scrubbing treatment, such that the liquid methanol stream from the first scrubbing will contain higher amounts of methyl acetate than liquid methanol streams obtained from subsequent scrubbing treatments.

The liquid solvent streams from a first and any subsequent scrubbing may be combined to form a single liquid stream.

Preferably, the temperature of a scrubbing solvent on entry into the scrubbing zone is from −50° C. to 100° C., more preferably from 0° C. to 60° C., most preferably from 35° C. to 55° C.

Preferably, a scrubbing solvent comprises methanol. The scrubbing solvent may be pure methanol. Alternatively, the scrubbing solvent may comprise a mixture of methanol and other components, such as a mixture of methanol and one or more of water and dimethyl ether. Mixtures of methanol and one or more of dimethyl ether and water for use as the scrubbing solvent may be obtained from the methanol synthesis product produced in the methanol synthesis reaction.

Suitably, the scrubbing solvent is selected from imported methanol, a methanol-rich stream recovered from the methanol synthesis product and mixtures thereof.

Suitably, all or a portion of the methanol-rich stream recovered from the methanol synthesis product is used as a scrubbing solvent.

Suitably, where multiple scrubbing treatments are employed, the scrubbing solvent for each scrubbing is a portion of the methanol-rich stream recovered from the methanol synthesis product.

Preferably, a scrubbing solvent which comprises a mixture of methanol and water contains water in an amount of less than 20 w/w %, more preferably less than 10 w/w %, and most preferably less than 5 w/w %.

Preferably, a scrubbing solvent which comprises a mixture of methanol and dimethyl ether contains dimethyl ether in an amount of less than 20 w/w %, more preferably less than 10 w/w %.

Dimethyl ether and acetic acid which may be present as components of the synthesis gas stream recovered from the carbonylation reaction product are generally absorbed in methanol-containing scrubbing solvents and consequently these components are removed together with methyl acetate as part of the liquid methanol solvent stream.

A liquid solvent stream comprising absorbed methyl acetate withdrawn from a scrubbing zone may be subject to processing and/or purification steps to recover the scrubbing solvent therefrom. Where at least a portion of, or substantially all of, the methanol-rich liquid stream is used as the liquid scrubbing solvent in one or more scrubbing units, the liquid methanol stream(s) containing absorbed methyl acetate (used methanol stream) may be passed to the dehydration-hydrolysis reaction zone for conversion therein to dimethyl ether and acetic acid.

In some or all embodiments of the present invention, at least a portion of the synthesis gas recovered from the carbonylation reaction product is subjected to multiple scrubbing treatments, such as two or more scrubbing treatments, in one scrubbing unit with a liquid scrubbing solvent. Suitably, the liquid solvent employed in each scrubbing treatment comprises, and preferably consists of, a portion of the methanol-rich stream recovered from the methanol synthesis product.

It is preferred to remove, in the one or more scrubbing treatments, at least 80%, preferably at least 90%, more preferably at least 95% and most preferably at least 99% of the methyl acetate from a synthesis gas.

Suitably, synthesis gas supplied to the methanol synthesis zone comprises methyl acetate in an amount 0 to 1 mol %, such as 0 to less than 1 mol %.

Scrubbing of a synthesis gas does not substantially alter the amounts of carbon monoxide, hydrogen and carbon dioxide contained therein. However, if one or more of carbon monoxide, hydrogen and carbon dioxide are present in the scrubbing solvent a portion of any such components may be released from the scrubbing solvent and form part of the scrubbed synthesis gas. In general however, the stoichiometric number of the scrubbed synthesis gas corresponds approximately to the stoichiometric number of the synthesis gas recovered from the carbonylation reaction product.

The stoichiometric number of the synthesis gas recovered from the carbonylation reaction product will depend principally upon the stoichiometric number of fresh synthesis gas used in the carbonylation reaction and the degree of conversion therein, but it may be adjusted by varying the amount of synthesis gas which is recovered from the carbonylation reaction product and recycled to the carbonylation reaction zone. The stoichiometric number of the scrubbed synthesis gas may therefore be adjusted so as to be optimal for methanol synthesis by altering one or more of these factors. Preferably, the scrubbed synthesis gas has a stoichiometric number optimised for methanol synthesis, that is, suitably in the range 1.5 to 2.5, such as 2.0 to 2.1, preferably 2.05.

Scrubbed synthesis gas depleted in methyl acetate can be directly passed to a methanol synthesis zone. Suitably, at least a portion of scrubbed synthesis gas is passed to the methanol synthesis zone for the production of methanol. If desired, the scrubbed synthesis gas in its entirety may be passed to the methanol synthesis zone.

If desired, all of the synthesis gas recovered from the carbonylation reaction product may be scrubbed. Alternatively, all of the recovered synthesis gas may be passed directly to the methanol synthesis zone without being subjected to a scrubbing treatment.

At least a portion of the synthesis gas recovered from the carbonylation reaction product is passed to a methanol synthesis zone. The recovered synthesis gas may be passed directly to the methanol synthesis zone. Alternatively, it may be passed to the methanol synthesis zone as scrubbed synthesis gas.

Preferably, at least a portion of the synthesis gas recovered from the carbonylation reaction product is recycled to the carbonylation reaction zone.

Suitably, synthesis gas recovered from the carbonylation reaction product is split into two portions, wherein a first portion is passed directly to the methanol synthesis zone or indirectly thereto via scrubbing and at least one other portion, which is, for example an equal portion, is recycled to the carbonylation reaction zone. Preferably, however, synthesis gas recovered from the carbonylation reaction product is split into a major portion and a minor portion. More preferably, the synthesis gas is split into a major portion and a minor portion, wherein the major portion is recycled to the carbonylation reaction zone and the minor portion is passed directly or indirectly via scrubbing to the methanol synthesis zone.

In an embodiment of the present invention, synthesis gas recovered from the carbonylation product is split into a major portion and a minor portion, wherein the major portion is recycled to the carbonylation reaction zone and the minor portion is scrubbed prior to being supplied to the methanol synthesis zone.

The relative amounts of synthesis gas recycled to the carbonylation reaction zone and synthesis gas passed to the methanol synthesis zone (directly or indirectly via scrubbing) can be varied. In particular, where it is desired to supply fresh synthesis gas to the methanol synthesis zone, the relative amount of synthesis gas recovered from the carbonylation reaction product and recycled to the carbonylation reactor, in general, will be significantly greater than that supplied to the methanol synthesis zone.

Suitably, and, in particular where fresh synthesis is not supplied to the methanol synthesis zone, the amount of synthesis gas recycled to the carbonylation reaction zone is at least 50 mol % of the synthesis gas recovered from the carbonylation reaction product, such as in the range 60 to 85 mol %, for example 70 to 80 mol %. Suitably, the amount of synthesis gas recovered from the carbonylation reaction product and passed to the methanol synthesis zone (directly or indirectly via scrubbing) is less than 50 mol %, such as in the range 10 to 30 mol %, for example 20 to 30 mol %.

In one embodiment of the present invention, 70 to 80 mol % of the synthesis gas recovered from the carbonylation reaction product is recycled to the carbonylation reaction zone and 20 to 30 mol % of the synthesis gas is passed directly or indirectly to the methanol synthesis zone.

In an embodiment of the present invention, 70 to 80 mol % of the synthesis gas recovered from the carbonylation reaction product is recycled to the carbonylation reaction zone and 20 to 30 mol % of the synthesis gas is scrubbed prior to being supplied to the methanol synthesis zone.

Preferably, where fresh synthesis gas is supplied to the methanol synthesis zone, the amount of synthesis gas recycled to the carbonylation reaction zone is at least 50 mol % of the synthesis gas recovered from the carbonylation reaction product, such as in the range 80 to 99 mol %, for example 95 to 98 mol %. Suitably, the amount of synthesis gas recovered from the carbonylation reaction product and passed to the methanol (directly or indirectly via scrubbing) is less than 50 mol %, such as in the range 1 to 20 mol %, for example 2 to 5 mol %.

In an embodiment of the present invention, 95 to 98 mol % of the synthesis gas recovered from the carbonylation reaction product is recycled to the carbonylation reaction zone and 2 to 5 mol % of the synthesis gas is passed directly or indirectly to the methanol synthesis zone.

Suitably, the synthesis gas may be compressed, in one or more compressors, prior to recycle to the carbonylation reaction zone.

If desired, a portion of the synthesis gas recovered from the carbonylation reaction product can be vented as purge gas but, preferably, substantially all of the recovered synthesis gas is recycled to the carbonylation reaction zone, or passed, directly or indirectly via scrubbing, to the methanol synthesis zone or a combination thereof.

The methanol synthesis process used to manufacture the methanol synthesis product of the present invention can be any suitable process. Commercially, methanol is produced by the catalytic conversion of carbon monoxide and hydrogen according to the overall equation $CO+2H_2 \rightleftharpoons CH_3OH$. The reaction proceeds in accordance with the following reactions:

$$CO_2+3H_2 \rightleftharpoons CH_3OH+H_2O \qquad (I)$$

$$H_2O+CO \rightleftharpoons CO_2+H_2 \qquad (II)$$

Conventionally, carbon monoxide and hydrogen required for methanol production is obtained from synthesis gas supplied directly to a methanol synthesis zone from reforming or partial oxidation processes.

In the present invention, synthesis gas recovered from the carbonylation reaction product and passed (directly or indirectly via scrubbing) to the methanol synthesis zone may be employed as the sole source of synthesis gas for methanol synthesis. However, as discussed above, it may be desirable to feed additional synthesis gas to the methanol synthesis zone, in particular where a synthesis gas feed to the carbonylation reaction zone has a low stoichiometric number. Additional sources of synthesis gas which may be fed to the methanol synthesis zone include one or more of fresh synthesis gas and at least a portion of synthesis gas recovered from the methanol synthesis product. Preferably, the amounts of the synthesis gas feeds passed to the methanol synthesis zone are adjusted for the approximately stoichiometric production of methanol. Preferably, the composition of the synthesis gas recovered from the carbonylation reaction product and one or more additional synthesis gas feeds to the methanol synthesis zone is such that the stoichiometric number is in the range 1.5 to 2.5, such as in the range 2.01 to 2.1, for example 2.05. Preferably, a feed of synthesis gas recovered from the carbonylation reaction product together with fresh synthesis gas has a stoichiometric number in the range 1.5 to 2.5, such as in the range 2.01 to 2.1, for example 2.05.

Synthesis gas recovered from the carbonylation reaction product, fresh synthesis and synthesis gas recovered from the methanol synthesis product may be passed to the methanol synthesis zone as separate feed streams. Preferably, however, one or more of these synthesis gas streams may be combined and passed to the methanol synthesis zone as a single combined feed stream.

Prior to use in the methanol synthesis zone, the synthesis gas feed(s) to the methanol synthesis zone may be heated, for example in one or more heat exchangers, to the desired methanol synthesis temperature.

In order for the methanol synthesis reaction to proceed favourably, the synthesis gas feed(s) to the methanol synthesis zone is preferably compressed to the desired methanol synthesis pressure.

The synthesis of methanol requires a source of carbon dioxide. Sources of carbon dioxide include synthesis gas, carbon dioxide generated in-situ during methanol synthesis and imported carbon dioxide. Carbon dioxide can be generated from water formed in the methanol synthesis process and by the addition of water to the methanol synthesis. However, there are a number of disadvantages associated with the addition of water to methanol synthesis for the in-situ generation of carbon dioxide, including the requirements for additional processing and the provision of a suitable source of water. However, if desired, at least one of water and imported carbon dioxide may be introduced into the methanol synthesis zone. Most desirably, all of the carbon dioxide required for methanol synthesis is derived from the synthesis gas feed to the carbonylation reaction, a fresh synthesis gas feed to the methanol synthesis zone or from in-situ generation from water formed in the methanol synthesis process.

Carbon dioxide which is unconsumed in the methanol synthesis is withdrawn from the methanol synthesis zone as part of the methanol synthesis product. If desired, carbon dioxide may be recovered from the methanol synthesis product, for example by conventional liquid/gas separation techniques.

In general, dimethyl ether does not take part in methanol synthesis and consequently, dimethyl ether which may be present in the synthesis gas passed to the methanol synthesis zone is withdrawn from the methanol synthesis zone as part of the methanol synthesis product.

Methanol synthesis is accomplished in the presence of a methanol synthesis catalyst. At least a portion of the synthesis gas recovered from the carbonylation reaction product, and optionally one or more of fresh synthesis gas and at least a portion of synthesis gas recovered from the methanol synthesis product, is contacted in the methanol synthesis zone with a methanol synthesis catalyst.

A number of catalysts active for methanol synthesis are known in the art and are also available commercially, for example, the commercial Katalco™ methanol synthesis catalysts available from Johnson Matthey plc. Typically the catalysts are based on copper and may also contain one or more additional metals such as zinc, magnesium and aluminium.

In one embodiment of this invention, the methanol synthesis catalyst comprises copper, zinc oxide and alumina.

The methanol synthesis catalyst may be employed in a fixed bed methanol synthesis zone, for example in the shape of pipes or tubes, where the synthesis gas recovered from the carbonylation reaction product and optionally one or more of fresh synthesis gas and synthesis gas recovered from the methanol synthesis product are passed over or through the methanol synthesis catalyst.

Preferably, methanol synthesis is carried out in the vapour phase.

Synthesis gas is contacted with a methanol synthesis catalyst under reactions conditions effective to effect the conversion of synthesis gas to form a methanol synthesis product comprising methanol and unconverted synthesis gas.

Suitably, methanol synthesis is carried out at a temperature of from 210° C. to 300° C., such as in the range of 210° C. to 270° C. or 220° C. to 300° C., for example in the range 230° C. to 275° C.

Preferably, methanol synthesis is carried out at a total pressure in the range 25 to 150 barg (2500 kPa to 15,000 kPa), for example in the range 50 to 100 barg (5000 kPa to 10,000 kPa).

Suitably, methanol synthesis is carried out at a temperature in the range 230° C. to 275° C. and at a total pressure in the range 50 to 100 barg (5000 kPa to 10,000 kPa).

In an embodiment of the present invention, methanol synthesis is carried out at a temperature of from 210° C. to 270° C. and at a total pressure in the range 50 to 100 barg (5000 kPa to 10,000 kPa).

In a preferred embodiment of the present invention, at least a portion of scrubbed synthesis gas, optionally combined with at least a portion of the synthesis gas recovered from the methanol synthesis product, is contacted with a methanol synthesis catalyst based on copper, preferably a catalyst comprising copper, zinc and aluminium, at a temperature in the range 220° C. to 300° C. or in the range 210° C. to 270° C. and at a total pressure in the range 25 to 150 barg (2500 kPa to 15,000 kPa).

Suitably, the total gas hourly space velocity of the total feed to the methanol synthesis zone (including any recycle synthesis gas, water and any imported carbon dioxide) is in the range 500 to 40,000 $h^{-1}$.

Contacting of synthesis gas recovered from the carbonylation reaction product, optionally with one or more of fresh synthesis gas and at least a portion of synthesis gas recovered from the methanol synthesis product, with the methanol synthesis catalyst produces a crude methanol synthesis product comprising methanol and unconverted synthesis gas. Depending on the exact nature of the components present in the synthesis gas feed(s) for methanol synthesis, the methanol synthesis product comprises methanol and unconverted synthesis gas and may comprise additional components, such as one or more of carbon dioxide, water and dimethyl ether.

The methanol synthesis product is withdrawn from the methanol synthesis zone, preferably in vapour form.

Methanol may be recovered from the withdrawn methanol synthesis product by known recovery techniques. Suitably, methanol may be recovered from at least a portion of the methanol synthesis product, for example by reducing the temperature of the methanol synthesis product to generate a cooled methanol-synthesis gas mixture. Suitably, the temperature of the mixture is reduced to a temperature in the range 30° C. to 50° C., preferably in the range 35° C. to 45° C. The cooled methanol-synthesis gas mixture is separated to recover a methanol-rich liquid stream and a synthesis gas stream.

Preferably, substantially all of the methanol synthesis product is separated to recover a methanol-rich liquid stream and a synthesis gas stream therefrom.

Separation of at least a portion of the methanol synthesis product may be carried out in one or more separation units. Each of the separation unit(s) may be of conventional design and may comprise one or more heat exchange means to cool the methanol synthesis product to condense out liquid methanol together with other condensable components such as water, from the methanol synthesis product, and one or more gas/liquid separation means such as a knock-out drum or a tangential inlet drum, to separate the cooled methanol-synthesis gas mixture to recover a methanol-rich liquid stream and a synthesis gas stream.

Alternatively, separation of the methanol synthesis product may be carried out directly in the methanol synthesis zone, that is, by withdrawing from the methanol synthesis zone one or more gaseous streams comprising synthesis gas and one or more liquid streams rich in methanol.

The methanol-rich liquid stream may comprise small amounts of water and unreacted dimethyl ether.

The methanol-rich liquid stream is suitable for use as a scrubbing solvent to scrub synthesis gas recovered from the carbonylation reaction product. Thus, preferably, at least a portion of, such as substantially all of the methanol-rich liquid stream is used as a scrubbing solvent. Advantageously, this avoids the need to import methanol or any other suitable solvent for use as a scrubbing solvent.

Where multiple scrubbing treatments are conducted, the methanol-rich liquid stream supplied to the scrubbing zone may be divided, and equal or unequal portions of the stream supplied to each of two or more scrubbing units in the scrubbing zone. For example, a minor portion of the methanol-rich liquid stream, such as >0 to 20%, may be supplied to a first scrubbing unit and a major portion of the stream, such as 80% to <100%, may be supplied to a second scrubbing unit.

Dimethyl ether which may be present in the methanol-rich liquid stream may be recovered therefrom, for example by distillation. The recovered dimethyl ether may be recycled to the carbonylation reaction zone.

Synthesis gas recovered from the methanol synthesis product may comprise carbon dioxide.

At least a portion of the synthesis gas recovered from the methanol synthesis product may be recycled to the methanol synthesis zone. Suitably, 90% to 99% of the synthesis gas may be recycled to the methanol synthesis zone.

If desired, to reduce the build-up of inert gases in the methanol synthesis zone, a portion of the synthesis gas recovered from the methanol synthesis product may be vented as a purge stream. Suitably, 1 to 10%, for example 1 to 5% of the synthesis gas recovered from the methanol synthesis product may be vented as a purge stream.

If desired, methanol may be recovered from one or more of, the methanol synthesis product withdrawn from the methanol synthesis zone, the methanol-rich liquid stream recovered from the methanol synthesis product and liquid solvent streams comprising methanol obtained from scrubbing of synthesis gas recovered from the carbonylation reaction product, by any conventional purification means, such as distillation, and sold as such. Alternatively, recovered methanol may be used, for example as a feedstock in a variety of chemical processes. Suitably, methanol may be carbonylated with carbon monoxide in the presence of a Group VIII noble metal catalyst, such as rhodium, iridium or mixtures thereof, to form acetic acid. Alternatively, methanol may be dehydrated in the presence of a suitable catalyst to form dimethyl ether. Suitable catalysts include aluminas, such as gamma-alumina.

In the present invention at least a portion of, and suitably substantially all of, of one or more of a methanol-rich liquid stream selected from a methanol-rich liquid stream recovered from the methanol synthesis product and a used methanol stream from a scrubbing zone is supplied to the dehydration-hydrolysis reaction zone and dehydrated therein in the presence of a suitable catalyst to generate dimethyl ether.

In an embodiment of the present invention, at least a portion of a used methanol stream from a scrubbing zone is supplied to the dehydration-hydrolysis reaction zone.

In a further embodiment of the present invention, at least a portion of a methanol-rich stream recovered from the methanol synthesis product is supplied to the dehydration-hydrolysis reaction zone.

In a yet further embodiment of the present invention, at least a portion of a methanol-rich stream recovered from the methanol synthesis product and at least a portion of a used methanol stream from a scrubbing zone is supplied to the dehydration-hydrolysis reaction zone.

At least a portion of, and suitably substantially all of, the methyl acetate-rich liquid stream recovered from the carbonylation reaction product is supplied to the dehydration-hydrolysis reaction zone and hydrolysed therein in the presence of a suitable catalyst to generate acetic acid.

A methanol-rich liquid stream and methyl acetate-rich liquid stream may be supplied to the dehydration-hydrolysis reaction zone as separate feeds or as a single combined feed.

The catalysts active for the dehydration of methanol to dimethyl ether may be the same or different to the catalyst active for the hydrolysis of methyl acetate to acetic acid.

Catalysts suitable for the dehydration of methanol to dimethyl ether are known, and include aluminas, such as gamma-alumina, zeolites, such as ZSM-5, mordenite and zeolites of framework structure type FER, as exemplified by ferrierite and ZSM-35.

Catalysts suitable for the hydrolysis of methyl acetate to acetate acid are known, and include heteropolyacids and salts thereof, for example ammonium salts of heteropolyacids, such as ammonium salts of a phosphotungstic acid or a silicotungstic acid, polymeric resins, such as those based on styrene divinylbenzene copolymers with sulphonic acid groups, for example Amberlyst™36WET (available from the Rohm & Haas Company), and zeolites, such as those of framework structure FER, as exemplified by ferrierite and ZSM-35.

Catalysts which are effective in catalysing both the hydrolysis of methyl acetate to acetic acid and the dehydration of methanol to dimethyl ether include zeolites and, in particular, zeolites which possess a 2-dimensional channel system comprising at least one channel defined by a 10-membered ring, such as zeolites of framework structure FER, as exemplified by ferrierite and ZSM-35. Such zeolites may be usefully employed in the present invention in their exchanged form with one or more alkali metal cations, such as cesium. Suitably, the catalyst for use in the dehydration-hydrolysis reaction zone is a ferrierite, preferably a ferrierite which is exchanged with cesium and has a silica:alumina molar ratio in the range 10:1 to 90:1.

A zeolite may be utilised as catalyst in the present invention in combination with a suitable binder material, such as an inorganic oxide binder, typically a silica, an alumina or a silica-alumina binder material.

Where it is desired to utilise more than one type of catalyst in the dehydration-hydrolysis reaction zone, such as an alumina catalyst and a zeolite catalyst, the catalysts may be utilised therein in the form of alternating catalyst beds or as one or more intimately mixed catalyst beds.

In the present invention, at least a portion of a methanol-rich liquid stream recovered from the methanol synthesis product or a scrubbing zone is employed as the source of methanol in the dehydration-hydrolysis reaction zone. However, if desired, additional methanol can be supplied to the dehydration-hydrolysis zone. Additional sources of methanol can include, for example recycle streams comprising methanol and methanol obtained from one or more of the dimethyl ether-rich product stream and the acetic acid-rich product stream. Other sources of additional methanol may include imported methanol. However, in general, it is not necessary to add imported methanol to the dehydration-hydrolysis reaction zone.

If desired, additional methyl acetate may also be supplied to the dehydration-hydrolysis reaction zone. Additional sources of methyl acetate can include, for example recycle streams comprising methyl acetate and methyl acetate separated from at least one of the dimethyl ether-rich product stream and the acetic acid-rich product stream. Other sources of additional methyl acetate may include imported methyl acetate. However, in general, it is not necessary to add imported methyl acetate to the dehydration-hydrolysis reaction zone.

Methanol and methyl acetate are contacted in the dehydration-hydrolysis reaction zone in any desired ratio, but suitably the molar ratio of methanol:methyl acetate is in the range 1:0.1 to 1:10, such as 1:0.2 to 1:5, for example 1:0.5 to 1:2.

In an embodiment of the present invention, the molar ratio of methanol:methyl acetate supplied to the dehydration-hydrolysis zone, including any recycle streams thereto, is 1:1 to 1:10, such as 1:1 to 1:5.

The hydrolysis of methyl acetate requires water as a reactant. Water is generated in-situ from the dehydration of methanol. Preferably, however, water is added to the dehydration-hydrolysis reaction zone. Water may be introduced into the dehydration-hydrolysis reaction zone as a component of one or more feed streams to the dehydration-hydrolysis reaction zone such as one or more of methyl acetate-rich, methanol-rich streams and recycle streams or it may be introduced as a separate additional stream.

The amount of water supplied to the dehydration-hydrolysis zone should not be so high as to substantially reduce catalytic performance. Suitably, water may be added in an amount in the range 0.1 to 50 mol %, preferably in the range 3 to 40 mol % and more preferably in the range 5 to 30 mol %, based on the total feed of methyl acetate, methanol and water to the dehydration-hydrolysis reaction zone.

A diluent such as an inert gas, for example nitrogen and helium, may also be supplied to the dehydration-hydrolysis reaction zone.

The dehydration-hydrolysis reaction may be carried out as a vapour phase process or as a liquid phase process, for example as a fixed bed process or a slurry phase process.

Methyl acetate-rich streams recovered from carbonylation reaction product and methanol-rich streams recovered from methanol synthesis product or scrubbing zone are in the liquid phase. Thus, where it is desired to operate the dehydration-hydrolysis reaction as a vapour phase process, it is preferable to volatilise these streams, for example, in a pre-heater prior to contact with the dehydration-hydrolysis catalyst(s).

The dehydration-hydrolysis reaction is suitably carried out by contacting methanol-rich and methyl acetate-rich streams with the catalyst at a temperature in the range 100° C. to 350° C. The dehydration-hydrolysis reaction may be carried out as a liquid phase process or as a vapour phase process. Liquid phase processes are preferably conducted at temperatures in the range 100° C. to 300° C., such as 140° C. to 210° C. Vapour phase processes are preferably conducted at temperatures in the range 150° C. to 350° C., such as 160° C. to 300° C.

The dehydration-hydrolysis reaction may be carried out at atmospheric pressure or at pressures greater than atmospheric. If the dehydration-hydrolysis reaction is desired to be carried out as a liquid phase process, it is preferred to operate the process at a total reaction pressure which is sufficient to maintain the dimethyl ether product in solution. Suitably, therefore, the pressure may be at least 40 barg, such as 40 to 100 barg. Where the dehydration-hydrolysis reaction is carried out as a vapour phase process, suitable operating pressures are in the range atmospheric to 30 barg (atmospheric to 3000 kPa), such as 5 to 20 barg (500 kPa to 2000 kPa).

In an embodiment, the dehydration-hydrolysis reaction is carried out in the liquid phase at a temperature in the range 100° C. to 300° C., such as 140° C. to 210° C. and at a pressure of at least 40 barg (4000 kPa), such as 40 to 100 barg (4000 kPa to 10,000 kPa).

In an embodiment, the dehydration-hydrolysis reaction is carried out in the vapour phase at a temperature in the range 150° C. to 350° C., such as 160° C. to 300° C. and at a pressure in the range atmospheric to 30 barg (atmospheric to 3000 kPa), such as 5 to 20 barg (500 kPa to 2000 kPa).

Suitably, the dehydration-hydrolysis reaction is carried out at a gas hourly space velocity (GHSV) is in the range 500 to 40,000 h$^{-1}$.

Suitably, the dehydration-hydrolysis reaction is carried out at a liquid hourly space velocity (LHSV) is in the range 0.2 to 20.

The dehydration-hydrolysis reaction product comprises acetic acid and dimethyl ether. Acetic acid-rich and dimethyl ether-rich product streams can be recovered from the dehydration-hydrolysis reaction product by any suitable process.

Suitably, the dehydration-hydrolysis reaction to form a reaction product comprising acetic acid and dimethyl ether and recovery of acetic acid-rich and dimethyl ether-rich product streams therefrom may be carried out by reactive distillation. Reactive distillation techniques and apparatus therefor are well-known. Typically, the methanol and methyl acetate-rich streams are supplied to conventional reactive distillation column, operated at, for example a pressure in the range atmospheric to 20 barg (atmospheric to 2000 kPa) and at a reaction temperature in the range 100° C. to 350° C., to produce a dehydration-hydrolysis reaction product, which dehydration-hydrolysis reaction product is inherently separated therein to produce a dimethyl ether-rich product stream, typically removed as an overhead, and an acetic acid-rich product stream, typically removed as a bottoms stream from the reactive distillation column.

Alternatively, where the dehydration-hydrolysis reaction is carried out in for example a fixed bed reactor or a slurry bed reactor, a dehydration-hydrolysis reaction product stream may be withdrawn therefrom.

Dimethyl ether has a low boiling point (−24° C.) and acetic acid has a high boiling point (118° C.). Thus, acetic acid-rich and dimethyl ether-rich product streams may be conveniently recovered from a withdrawn dehydration-hydrolysis reaction product by conventional purification methods, such as by distillation in one or more conventional distillation columns.

Suitably, a distillation column may be a tray or packed column. The temperatures and pressures employed in the columns may vary. Suitably, a distillation column may be operated at a pressure, for example in the range from atmospheric to 20 barg.

Temperatures within a distillation column will normally range between the boiling points of the components removed as the overhead and the boiling point of the components removed as a bottoms fraction. As will be recognized by those skilled in the art, the temperature at a given point in a distillation column is dependent on the composition of the material at that point and the pressure of the column. Suitably, a distillation column may be operated at temperatures in the range 25° C. to 200° C., for example at a base temperature, such as in the range 110° C. to 200° C. and at a heads temperature, such as in the range 25° C. to 100° C. The dimethyl ether-rich product stream is generally recovered as an overhead from a distillation column, and the acetic acid-rich product stream will typically be recovered as a bottoms fraction from a distillation column.

Suitably, at least a portion of, and preferably substantially all of the dimethyl ether-rich product stream is recycled to the carbonylation reaction zone. Advantageously, such recycle reduces the amount of fresh dimethyl ether to be supplied to the carbonylation reaction zone. More advantageously, recycling dimethyl ether to the carbonylation reaction zone allows the production of acetic acid from a single synthesis gas feed together with a reduction in fresh dimethyl ether requirements.

The dehydration of methanol and the hydrolysis of methyl acetate are equilibrium reactions, and therefore, in addition to acetic acid and dimethyl ether, the dehydration-hydrolysis reaction product generally also comprises one or more of unreacted methanol and unreacted methyl acetate. Typically, the dehydration-hydrolysis reaction product also comprises water. Thus, one or both of the acetic acid-rich and dimethyl ether-rich streams recovered from the dehydration-hydrolysis reaction product may also comprise one or more of methanol, methyl acetate and water.

The present invention may further comprise the recovery of one or more components selected from methanol, methyl acetate and water from at least a portion of one or more of the acetic acid-rich product stream and the dimethyl ether-rich product stream and recycling the one or more recovered components to the dehydration-hydrolysis reaction zone.

Methanol, methyl acetate and water may be recovered from one or both of the acetic acid-rich stream and dimethyl ether-rich streams to obtain purified acetic acid and purified dimethyl ether respectively, for example by conventional purification processes, such as by distillation in one or more distillation columns.

The purified dimethyl ether may be sold or used as a fuel or as a feedstock to chemical processes, including use as a feed to the carbonylation reaction zone of the present invention.

The purified acetic acid may be sold or may be used as a feedstock in a variety of chemical processes, such as the manufacture of vinyl acetate or ethyl acetate.

The integrated process of the present invention may be operated as a continuous process or as a batch process preferably, operated as a continuous process.

FIG. 1 is a block diagram showing one embodiment of the present invention of an integrated process for the production of acetic acid. The integrated unit 110 includes a synthesis gas feed line 112 and a dimethyl ether feed line 114 connected to a carbonylation reactor 116. In use, fresh synthesis gas is heated to the desired carbonylation reaction temperature and fed to the carbonylation reactor 116 via the synthesis gas feed line 112. The synthesis gas comprises carbon monoxide, hydrogen and optionally carbon dioxide and, preferably, has a stoichiometric number in the range 0.9 to 1.3. Dry dimethyl ether is supplied to the carbonylation reactor 116 via the dimethyl ether feed line 114, which joins the synthesis gas feed line 112 before entry to the carbonylation reactor 116. The carbonylation reactor 116 contains a catalyst active for the carbonylation of dimethyl ether to methyl acetate, for example a mordenite zeolite, suitably mordenite in its hydrogen form. The dimethyl ether and synthesis gas are contacted with the catalyst in the carbonylation reactor 116 at a temperature in the range 250° C. to 350° C. and a total pressure in the range 10 to 100 barg (1000 kPa to 10,000 kPa) to form a gaseous carbonylation reaction product comprising methyl acetate and synthesis gas enriched in hydrogen which is withdrawn from the carbonylation reactor 116 via a carbonylation reaction product line 118 and passed to a first separation unit 120 comprising, for example, a heat exchanger and knock-out drum. In separation unit 120, the carbonylation reaction product is cooled, suitably to a temperature in the range 40° C. to 50° C., and a methyl acetate-rich liquid stream and a synthesis gas stream are recovered therefrom. The methyl acetate-rich liquid stream is removed from the separation unit 120 via a methyl acetate liquid line 122. The synthesis gas is removed from the first separation unit 120 via a first synthesis gas line 124. The first synthesis gas line 124 is connected to a methanol synthesis reactor 126 and, optionally, all of the synthesis gas recovered from the first separation unit 120 is heated in one or more heat exchangers (not shown) to the desired methanol synthesis temperature and passed to the methanol synthesis reactor 126. Alternatively, the synthesis gas recovered from the separation unit 120 is split into two portions, a first portion of the synthesis gas, such as 60 to 85 mol % thereof, is optionally compressed to the carbonylation reaction pressure in one or more compressors (not shown) and recycled to the carbonylation reactor 116 via an optional first synthesis gas recycle line 128, and a second portion is heated in one or more heat exchangers to the desired methanol synthesis temperature (not shown) and passed to the methanol synthesis reactor 126. The methanol synthesis reactor 126 contains a catalyst active for the production of methanol, for example a commercial copper-containing methanol synthesis catalyst, for example a Katalco™ catalyst available from Johnson Matthey plc. The synthesis gas passed to the methanol synthesis reactor 126 is contacted with the catalyst therein under methanol synthesis conditions, such as at a temperature in the range 230° C. to 275° C. and at a total pressure in the range 50 to 100 barg (5000 kPa to 10,000 kPa), to generate a methanol synthesis product comprising methanol and unconverted synthesis gas. The methanol synthesis product is withdrawn from the methanol synthesis reactor 126 via a methanol synthesis product line 130, and is supplied to a second separation unit 132 which comprises, for example, a heat exchanger and a knock-out drum, where it is cooled, suitably to a temperature in the range 30° C. to 50° C., and separated to recover a methanol-rich liquid stream and a synthesis gas stream. The methanol-rich liquid stream is removed from the second separation unit 132 via a methanol liquid line 134, and the synthesis gas is removed from the second separation unit 132 via a second synthesis gas line 136. The synthesis gas may be vented as a purge stream or all or part of it, such as 90 to 99% thereof, may be recycled to the methanol synthesis reactor 126 via an optional second synthesis gas recycle line 138. The methyl acetate-rich liquid stream removed from the first separation unit 120 via the methyl-acetate liquid line 122, and the methanol-rich liquid stream removed from the second separation unit 132 via methanol liquid line 134 are combined, optionally volatilised to the vapour phase, for example in a pre-heater (not shown), and supplied to a dehydration-hydrolysis reactor 140. The reactor 140 contains at least one catalyst active for the dehydration of methanol and active for the hydrolysis of methyl acetate, for example a zeolite, such as ferrierite. Water, suitably in an amount of 0.1 to 50 mol % based on the total feed to the reactor 140, is supplied to the dehydration-hydrolysis reactor 140 via a water feed line 150. The methanol and methyl acetate are converted in the dehydration-hydrolysis reactor 140 under dehydration-hydrolysis reaction conditions, suitably at a temperature in the range 100° C. to 350° C. and at atmospheric or greater pressure, to a dehydration-hydrolysis reaction product comprising dimethyl ether and acetic acid, which reaction product is withdrawn from the dehydration-hydrolysis reactor 140 via a dehydration-hydrolysis reaction product line 142. The dehydration-hydrolysis reaction product is supplied to a third separation unit 144 comprising, for example, one or more distillation columns, suitably operated at a temperature in the range 25° C. to 200° C. and at a pressure in the range atmospheric to 30 barg, to recover an acetic acid-rich stream and a dimethyl ether-rich stream. The acetic acid-rich stream is removed from the third separation unit 144, typically as a bottoms stream, via an acetic acid removal line 146. The dimethyl ether-rich stream is removed from the third separation unit 144, typically as an overhead stream, via a dimethyl ether removal line 148. Both the acetic acid-rich stream and the dimethyl ether-rich stream may also comprise varying amounts of methanol, methyl acetate and water, and these may optionally be removed from the streams and recycled to the dehydration-hydrolysis reactor 140 (not shown).

Figure 2:
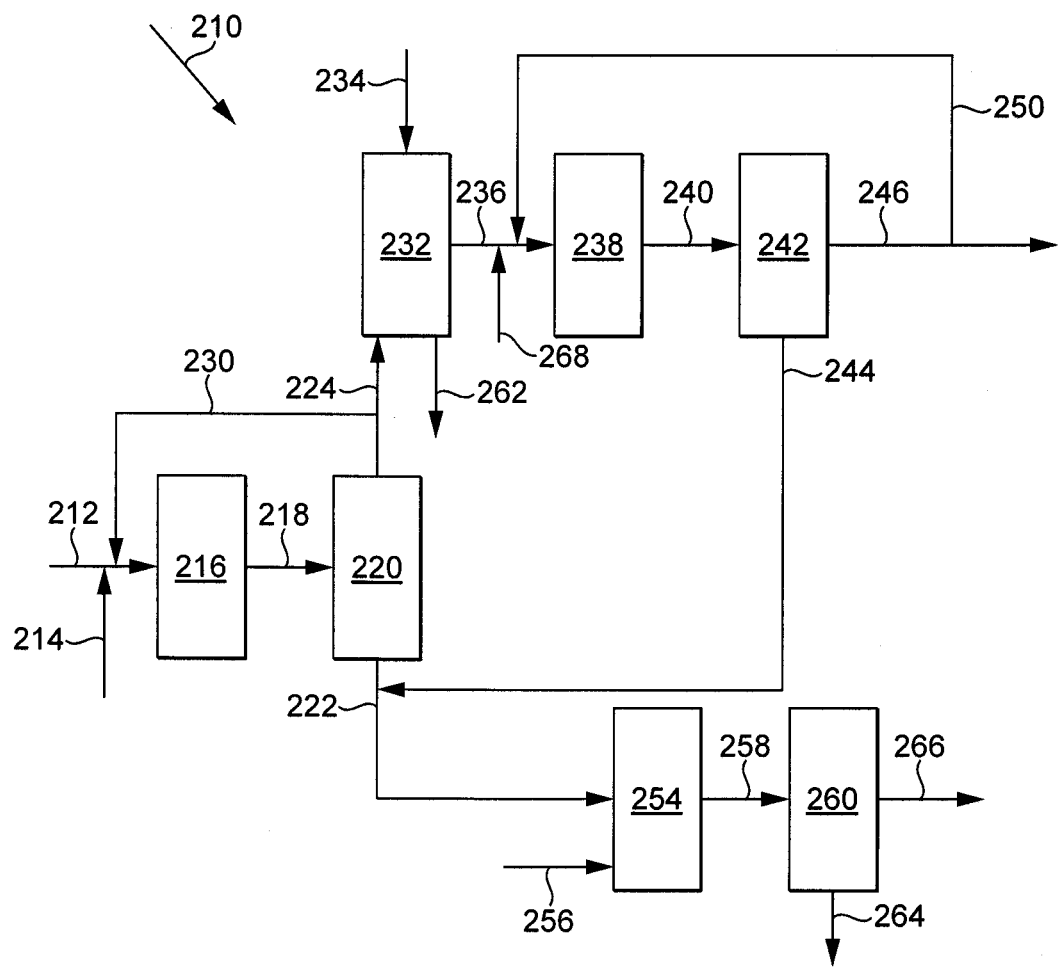
FIG. 2 is a block diagram showing an embodiment of the present invention of an integrated process for the production of acetic acid incorporating fresh synthesis gas feeds to carbonylation and methanol synthesis and scrubbing of synthesis gas for methanol synthesis.

FIG. 2 is a block diagram showing an embodiment of the present invention of an integrated process for the production of acetic acid incorporating fresh synthesis gas feeds to carbonylation and methanol synthesis and scrubbing of synthesis gas for methanol synthesis. The integrated unit 210 includes a synthesis gas feed line 212 and a dimethyl ether feed line 214 connected to a carbonylation reactor 216. In use, a first fresh synthesis gas is heated to the desired carbonylation reaction temperature and fed to the carbonylation reactor 216 via the synthesis gas feed line 212. The synthesis gas comprises carbon monoxide, hydrogen and carbon dioxide and, preferably, has a stoichiometric number, in the range 0.05 to 1.1. Dry dimethyl ether is supplied to the carbonylation reactor 216 via the dimethyl ether feed line 214, which joins the synthesis gas feed line 212 before entry to the carbonylation reactor 216. The carbonylation reactor 216 contains a catalyst active for the carbonylation of dimethyl ether to methyl acetate, for example a mordenite zeolite, suitably mordenite in its hydrogen form. The dimethyl ether and synthesis gas are contacted with the catalyst in the carbonylation reactor 216 at a temperature in the range 250° C. to 350° C. and a total pressure in the range 10 to 100 barg to form a gaseous carbonylation reaction product comprising methyl acetate and synthesis gas enriched in hydrogen which is withdrawn from the carbonylation reactor 216 via a carbonylation reaction product line 218 and passed to a first separation unit 220 comprising, for example, a heat exchanger and knock-out drum. In separation unit 220, the carbonylation reaction product is cooled, suitably to a temperature in the range 40° C. to 50° C., and a methyl acetate-rich liquid stream and a synthesis gas stream comprising a small amount of methyl acetate, for example an amount in the range 0.1 to 5 mol %, are recovered therefrom. The methyl acetate-rich liquid stream is removed from the separation unit 220 via a methyl acetate liquid line 222. The synthesis gas is removed from the first separation unit 220 via a first synthesis gas line 224 and is divided into a first part and a second part, for example by a suitable valve system. The first part of the synthesis gas, suitably comprising 1 to 20 mol % thereof, is supplied to a scrubbing unit 232. The second part of the synthesis gas, suitably comprising 80 to 99 mol % thereof, is recycled to the carbonylation reactor 216 via a first synthesis gas recycle line 230. The scrubbing unit 232 is supplied, for example with a counter-current flow of liquid scrubbing solvent, suitably comprising methanol, via a solvent feed line 234, and the synthesis gas comprising methyl acetate passed to the scrubbing unit 232 is contacted therein with the liquid scrubbing solvent to remove methyl acetate. The liquid scrubbing solvent containing absorbed methyl acetate and other components soluble in the solvent, for example dimethyl ether and acetic acid, is removed from the scrubbing unit 232 via a solvent removal line 262, and the scrubbed synthesis gas depleted in methyl acetate is removed via a scrubbed synthesis gas line 236 and fed to a methanol synthesis reactor 238. A second fresh synthesis gas comprising carbon monoxide, hydrogen and carbon dioxide is supplied to the methanol synthesis reactor 238 via a second synthesis gas feed line 268. The second synthesis gas feed line 268 joins the scrubbed synthesis gas line 236, and the combined feed is heated in one or more heat exchangers to the desired methanol synthesis temperature (not shown) and passed to the methanol synthesis reactor 238. The methanol synthesis reactor 238 contains a catalyst active for the production of methanol, for example a commercial copper-containing methanol synthesis catalyst, for example a Katalco™ catalyst available from Johnson Matthey plc. The combined synthesis gas passed to the methanol synthesis reactor 238 is contacted with the catalyst therein under methanol synthesis conditions, such as at a temperature in the range 230° C. to 275° C. and at a total pressure in the range 50 to 100 barg (5000 kPa to 10,000 kPa), to generate a methanol synthesis product comprising methanol and unconverted synthesis gas. The methanol synthesis product is withdrawn from the methanol synthesis reactor 238 via a methanol synthesis product line 240, and is supplied to a second separation unit 242 which comprises, for example, a heat exchanger and a knock-out drum, where it is cooled, suitably to a temperature in the range 30° C. to 50° C., and separated to recover a methanol-rich liquid stream and a synthesis gas stream. The methanol-rich liquid stream is removed from the second separation unit 242 via a methanol liquid line 244, and the synthesis gas is removed from the second separation unit 242 via a second synthesis gas line 246. The synthesis gas is divided, for example by a suitable valve system, into a first portion suitably comprising 90% to 99% of the synthesis gas, and a second portion suitably comprising 1% to 10% of the synthesis gas. The first portion of the synthesis gas is recycled to the methanol synthesis reactor 238 via a second synthesis gas recycle line 250, which connects to the scrubbed synthesis gas line 236, so that the first portion of the synthesis gas is combined with the scrubbed synthesis gas and the fresh synthesis gas prior to supply to the methanol synthesis reactor 238. The second portion of the synthesis gas is removed as a purge stream. The methyl acetate-rich liquid stream removed from the first separation unit 220 via the methyl-acetate liquid line 222, and the methanol-rich liquid stream removed from the second separation unit 242 via methanol liquid line 244 are combined, optionally volatilised to the vapour phase, for example in a pre-heater (not shown), and supplied to a dehydration-hydrolysis reactor 254. The dehydration hydrolysis reactor 254 contains at least one catalyst active for the dehydration of methanol and active for the hydrolysis of methyl acetate, for example a zeolite, such as ferrierite. Water, suitably in an amount of 0.1 to 50 mol % based on the total feed to the dehydration-hydrolysis reactor 254, is supplied to the reactor 254 via a water feed line 256. The methanol and methyl acetate are converted in the dehydration-hydrolysis reactor 254 under dehydration-hydrolysis reaction conditions, suitably at a temperature in the range 100° C. to 350° C. and at atmospheric or greater pressure, to a dehydration-hydrolysis reaction product comprising dimethyl ether and acetic acid, which reaction product is withdrawn from the dehydration-hydrolysis reactor 254 via a dehydration-hydrolysis reaction product line 258. The dehydration-hydrolysis reaction product is supplied to a third separation unit 260 comprising, for example, one or more distillation columns, suitably operated at a temperature in the range 25° C. to 200° C. and at a pressure in the range atmospheric to 30 barg (atmospheric to 3000 kPa), to recover an acetic acid-rich stream and a dimethyl ether-rich stream. The acetic acid-rich stream is removed from the third separation unit 260, typically as a bottoms stream, via an acetic acid removal line 264. The dimethyl ether-rich stream is removed from the third separation unit 260, typically as an overhead stream, via a dimethyl ether removal line 266. Both the acetic acid-rich stream and the dimethyl ether-rich stream may also comprise varying amounts of methanol, methyl acetate and water, and these may optionally be removed from the streams and recycled to the dehydration-hydrolysis reactor 254 (not shown).

Figure 3:
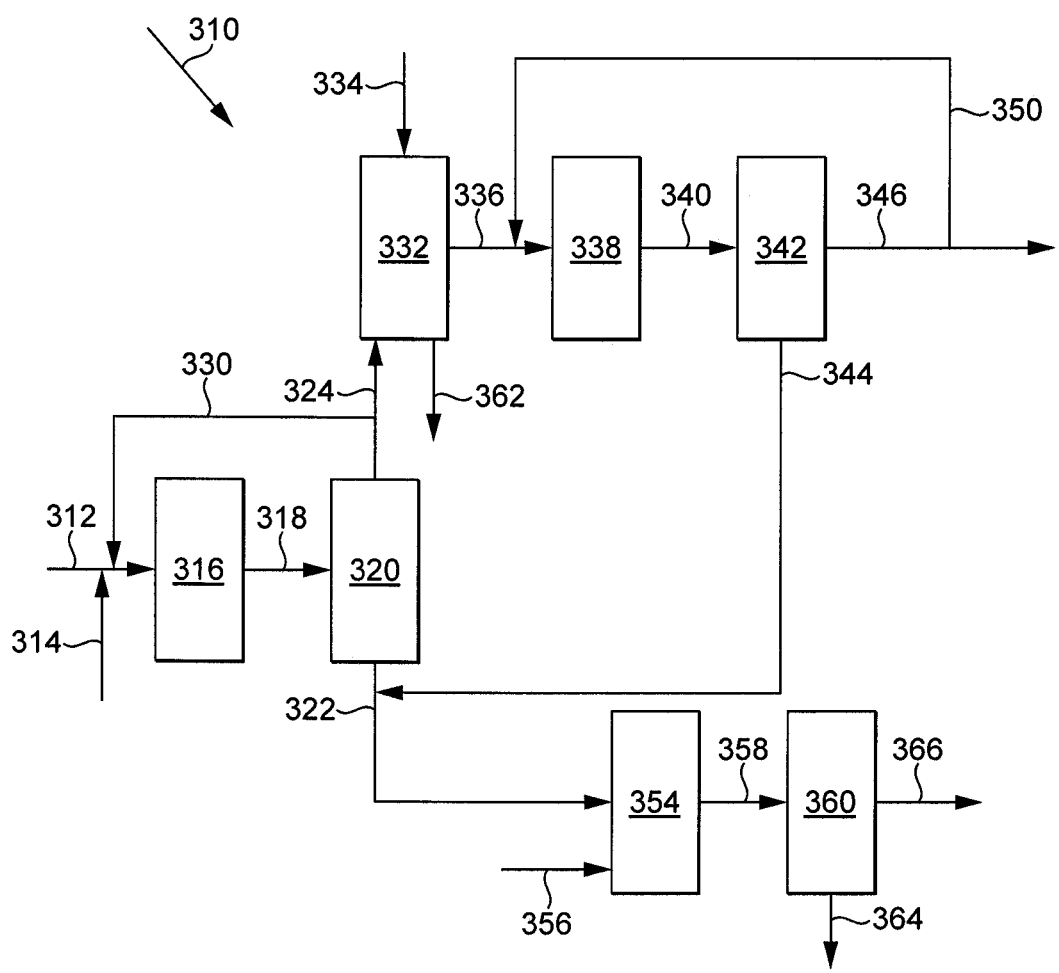
FIG. 3 is a block diagram showing an embodiment of the present invention of an integrated process for the production of acetic acid incorporating scrubbing of synthesis gas feed for methanol synthesis.

FIG. 3 is a block diagram showing an embodiment of the present invention of an integrated process for the production of acetic acid incorporating scrubbing of synthesis gas feed for methanol synthesis. The integrated unit 310 includes a synthesis gas feed line 312 and a dimethyl ether feed line 314 connected to a carbonylation reactor 316. In use, a fresh synthesis gas is heated to the desired carbonylation reaction temperature and fed to the carbonylation reactor 316 via the synthesis gas feed line 312. The synthesis gas comprises carbon monoxide, hydrogen and carbon dioxide and, preferably, has a stoichiometric number, in the range 0.9 to 1.3 Dry dimethyl ether is supplied to the carbonylation reactor 316 via the dimethyl ether feed line 314, which joins the synthesis gas feed line 312 before entry to the carbonylation reactor 316. The carbonylation reactor 316 contains a catalyst active for the carbonylation of dimethyl ether to methyl acetate, for example a mordenite zeolite, suitably mordenite in its hydrogen form. The dimethyl ether and synthesis gas are contacted with the catalyst in the carbonylation reactor 316 at a temperature in the range 250° C. to 350° C. and a total pressure in the range 10 to 100 barg (1000 kPa to 10,000 kPa) to form a gaseous carbonylation reaction product comprising methyl acetate and synthesis gas enriched in hydrogen which is withdrawn from the carbonylation reactor 316 via a carbonylation reaction product line 318 and passed to a first separation unit 320 comprising, for example, a heat exchanger and knock-out drum. In separation unit 320, the carbonylation reaction product is cooled, suitably to a temperature in the range 40° C. to 50° C., and a methyl acetate-rich liquid stream and a synthesis gas stream comprising a small amount of methyl acetate, for example an amount in the range 0.1 to 5 mol %, are recovered therefrom. The methyl acetate-rich liquid stream is removed from the separation unit 320 via a methyl acetate liquid line 322. The synthesis gas is removed from the first separation unit 320 via a first synthesis gas line 324 and is divided into a first part and a second part, for example by a suitable valve system. The first part of the synthesis gas, suitably comprising 20 to 30% thereof, is supplied to a scrubbing unit 332. The second part of the synthesis gas, suitably comprising 70 to 80% thereof, is recycled to the carbonylation reactor 316 via a first synthesis gas recycle line 330. The scrubbing unit 332 is supplied, for example, with a counter-current flow of liquid scrubbing solvent, suitably comprising methanol, via a solvent feed line 334, and the synthesis gas comprising methyl acetate passed to the scrubbing unit 332 is contacted therein with the liquid scrubbing solvent to remove methyl acetate. The liquid scrubbing solvent containing absorbed methyl acetate and other components soluble in the solvent, suitably dimethyl ether and acetic acid, is removed from the scrubbing unit 332 via a solvent removal line 362, and the scrubbed synthesis gas depleted in methyl acetate is removed via a scrubbed synthesis gas line 336 and fed to a methanol synthesis reactor 338. The methanol synthesis reactor 338 contains a catalyst active for the production of methanol, for example a commercial copper-containing methanol synthesis catalyst, for example a Katalco™ catalyst available from Johnson Matthey plc. Recycle synthesis gas recovered from the methanol synthesis product is combined with the scrubbed synthesis gas via recycle synthesis gas line 350. The combined synthesis gas is heated in one or more heat exchangers to the desired methanol synthesis temperature (not shown) and passed to the methanol synthesis reactor 338 and contacted therein with the catalyst under methanol synthesis conditions, such as at a temperature in the range 230° C. to 275° C. and at a total pressure in the range 50 to 100 barg (5000 kPa to 10,000 barg) to generate a methanol synthesis product comprising methanol and unconverted synthesis gas. The methanol synthesis product is withdrawn from the methanol synthesis reactor 338 via a methanol synthesis product line 340, and is supplied to a second separation unit 342 which comprises, for example, a heat exchanger and a knock-out drum, where it is cooled, suitably to a temperature in the range 30° C. to 50° C., and separated to recover a methanol-rich liquid stream and a synthesis gas stream. The methanol-rich liquid stream is removed from the second separation unit 342 via a methanol liquid line 344, and the synthesis gas is removed from the second separation unit 342 via a second synthesis gas line 346. The synthesis gas is divided, for example by a suitable valve system, into a first portion suitably comprising 90 to 99% of the synthesis gas, and a second portion suitably comprising 1 to 10% of the synthesis gas. The first portion of the synthesis gas is recycled to the methanol synthesis reactor 338 via a second synthesis gas recycle line 350, which connects to the scrubbed synthesis gas line 336. The second portion of the synthesis gas is removed as a purge stream. The methyl acetate-rich liquid stream removed from the first separation unit 320 via the methyl-acetate liquid line 322, and the methanol-rich liquid stream removed from the second separation unit 342 via methanol liquid line 344, are combined, optionally volatilised to the vapour phase, for example in a pre-heater (not shown), and supplied to a dehydration-hydrolysis reactor 354. The reactor 354 contains at least one catalyst active for the dehydration of methanol and active for the hydrolysis of methyl acetate, for example a zeolite, such as ferrierite. Water, suitably in an amount of 0.1 to 50 mol % based on the total feed to the dehydration-hydrolysis reactor 354, is supplied to the reactor 354 via a water feed line 356. The methanol and methyl acetate are converted in the dehydration-hydrolysis reactor 354 under dehydration-hydrolysis reaction conditions, suitably at a temperature in the range 100 to 350° C. and at atmospheric or greater pressure, to a dehydration-hydrolysis reaction product comprising dimethyl ether and acetic acid, which reaction product is withdrawn from the dehydration-hydrolysis reactor 354 via a dehydration-hydrolysis reaction product line 358. The dehydration-hydrolysis reaction product is supplied to a third separation unit 360 comprising, for example, one or more distillation columns, suitably operated at a temperature in the range 25° C. to 200° C. and at a pressure in the range atmospheric to 30 barg (atmospheric to 3000 kPa), to recover an acetic acid-rich stream and a dimethyl ether-rich stream. The acetic acid-rich stream is removed from the third separation unit 360, typically as a bottoms stream, via an acetic acid removal line 364. The dimethyl ether-rich stream is removed from the third separation unit 360, typically as an overhead stream, via a dimethyl ether removal line 366. Both the acetic acid-rich stream and the dimethyl ether-rich stream may also comprise varying amounts of methanol, methyl acetate and water, and these may optionally be removed from the streams and recycled to the dehydration-hydrolysis reactor 354 (not shown).

Figure 4:
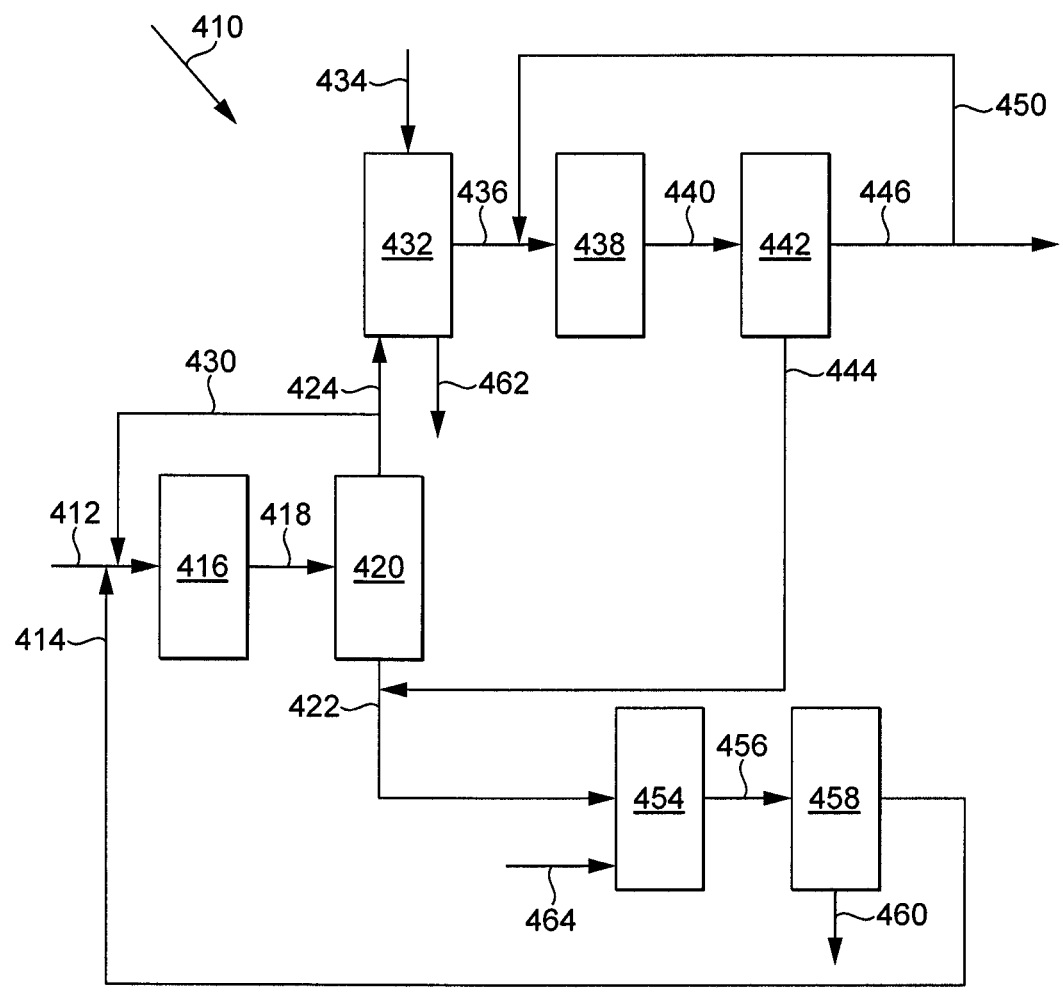
FIG. 4 is a block diagram showing an embodiment of the present invention of an integrated process for the production of acetic acid and incorporating scrubbing of synthesis gas feed for methanol synthesis and recycle of dimethyl ether for carbonylation.

FIG. 4 is a block diagram showing an embodiment of the present invention of an integrated process for the production of acetic acid and incorporating scrubbing of synthesis gas feed for methanol synthesis and recycle of dimethyl ether for carbonylation. The integrated unit 410 includes a synthesis gas feed line 412 and a dimethyl ether feed line 414 connected to a carbonylation reactor 416. In use, a fresh synthesis gas is heated to the desired carbonylation reaction temperature and fed to the carbonylation reactor 416 via the synthesis gas feed line 412. The synthesis gas comprises carbon monoxide, hydrogen and carbon dioxide and, preferably, has a stoichiometric number in the range 0.9 to 1.3. Dry fresh dimethyl ether is supplied to the carbonylation reactor 416 (not shown) and recycle dimethyl ether is supplied to the carbonylation reactor via feed line 414, which joins the synthesis gas feed line 412 before entry to the carbonylation reactor 416. The carbonylation reactor 416 contains a catalyst active for the carbonylation of dimethyl ether to methyl acetate, for example a mordenite zeolite, suitably mordenite in its hydrogen form. The dimethyl ether and synthesis gas are contacted with the catalyst in the carbonylation reactor 416 at a temperature in the range 250° C. to 350° C. and a total pressure in the range 10 to 100 barg (1000 kPa to 10,000 kPa) to form a gaseous carbonylation reaction product comprising methyl acetate and synthesis gas enriched in hydrogen which is withdrawn from the carbonylation reactor 416 via a carbonylation reaction product line 418 and passed to a first separation unit 420 comprising, for example, a heat exchanger and knock-out drum. In separation unit 420, the carbonylation reaction product is cooled, suitably to a temperature in the range 40° C. to 50° C., and a methyl acetate-rich liquid stream and a synthesis gas stream comprising a small amount of methyl acetate, for example an amount in the range 0.1 to 5 mol %, are recovered therefrom. The methyl acetate-rich liquid stream is removed from the separation unit 420 via a methyl acetate liquid line 422. The synthesis gas is removed from the first separation unit 420 via a first synthesis gas line 424 and is divided into a first part and a second part, for example by a suitable valve system. The first part of the synthesis gas, suitably comprising 20 to 30% thereof, is supplied to a scrubbing unit 432. The second part of the synthesis gas, suitably comprising 70 to 80% thereof, is recycled to the carbonylation reactor 416 via a first synthesis gas recycle line 430. The scrubbing unit 432 is supplied, for example, with a counter-current flow of liquid scrubbing solvent, suitably comprising methanol, via a solvent feed line 434, and the synthesis gas comprising methyl acetate passed to the scrubbing unit 432 is contacted therein with the liquid scrubbing solvent to remove methyl acetate. The liquid scrubbing solvent containing absorbed methyl acetate and other components soluble in the solvent, suitably dimethyl ether and acetic acid, is removed from the scrubbing unit 432 via a solvent removal line 462, and the scrubbed synthesis gas depleted in methyl acetate is removed via a scrubbed synthesis gas line 436 before being fed to a methanol synthesis reactor 438. The methanol synthesis reactor 438 contains a catalyst active for the production of methanol, for example a commercial copper-containing methanol synthesis catalyst, for example a Katalco™ catalyst available from Johnson Matthey plc. Recycle synthesis gas recovered from the methanol synthesis product is combined with the scrubbed synthesis gas via recycle synthesis gas line 450. The combined synthesis gas is heated in one or more heat exchangers to the desired methanol synthesis temperature (not shown) and passed to the methanol synthesis reactor 438, and contacted therein with the catalyst under methanol synthesis conditions, such as at a temperature in the range 230° C. to 275° C. and at a total pressure in the range 50 to 100 barg (5000 kPa to 10,000 kPa), to generate a methanol synthesis product comprising methanol and unconverted synthesis gas. The methanol synthesis product is withdrawn from the methanol synthesis reactor 438 via a methanol synthesis product line 440, and is supplied to a second separation unit 442 which comprises, for example, a heat exchanger and a knock-out drum, where it is cooled, suitably to a temperature in the range 30° C. to 50° C., and separated to recover a methanol-rich liquid stream and a synthesis gas stream. The methanol-rich liquid stream is removed from the second separation unit 442 via a methanol liquid line 444, and the synthesis gas is removed from the second separation unit 442 via a second synthesis gas line 446. The synthesis gas is divided, for example by a suitable valve system, into a first portion suitably comprising 90 to 99% of the synthesis gas, and a second portion suitably comprising 1 to 10% of the synthesis gas. The first portion of the synthesis gas is recycled to the methanol synthesis reactor 438 via second synthesis gas recycle line 450, which connects to the scrubbed synthesis gas line 436. The second portion of the synthesis gas is removed as a purge stream. The methyl acetate-rich liquid stream removed from the first separation unit 420 via the methyl-acetate liquid line 422, and the methanol-rich liquid stream removed from the second separation unit 442 via methanol liquid line 444 are combined, optionally volatilised to the vapour phase, for example in a pre-heater (not shown), and supplied to a dehydration-hydrolysis reactor 454. The dehydration-hydrolysis reactor 454 contains at least one catalyst active for the dehydration of methanol and active for the hydrolysis of methyl acetate, for example a zeolite, such as ferrierite. Water, suitably in an amount of 0.1 to 50 mol % based on the total feed to the dehydration-hydrolysis reactor 454, is supplied to the reactor 454 via a water feed line 464. The methanol and methyl acetate are converted in the dehydration-hydrolysis reactor 454 under dehydration-hydrolysis reaction conditions, suitably at a temperature in the range 100° C. to 350° C. and at atmospheric or greater pressure, to a dehydration-hydrolysis reaction product comprising dimethyl ether and acetic acid, which reaction product is withdrawn from the dehydration-hydrolysis reactor 454 via a dehydration-hydrolysis reaction product line 456. The dehydration-hydrolysis reaction product is supplied to a third separation unit 458 comprising, for example, one or more distillation columns, suitably operated at a temperature in the range 25° C. to 200° C. and at a pressure in the range atmospheric to 30 barg (atmospheric to 3000 kPa), to recover an acetic acid-rich stream and a dimethyl ether-rich stream. The acetic acid-rich stream is removed from the third separation unit 458, typically as a bottoms stream, via an acetic acid removal line 460. The dimethyl ether-rich stream is removed from the third separation unit 458, typically as an overhead stream, via the dimethyl ether feed line 414 and recycled to the carbonylation reactor 416. Both the acetic acid-rich stream and the dimethyl ether-rich stream may also comprise varying amounts of methanol, methyl acetate and water, and these may optionally be removed from the streams and recycled to the dehydration-hydrolysis reactor 454 (not shown).

Figure 5:
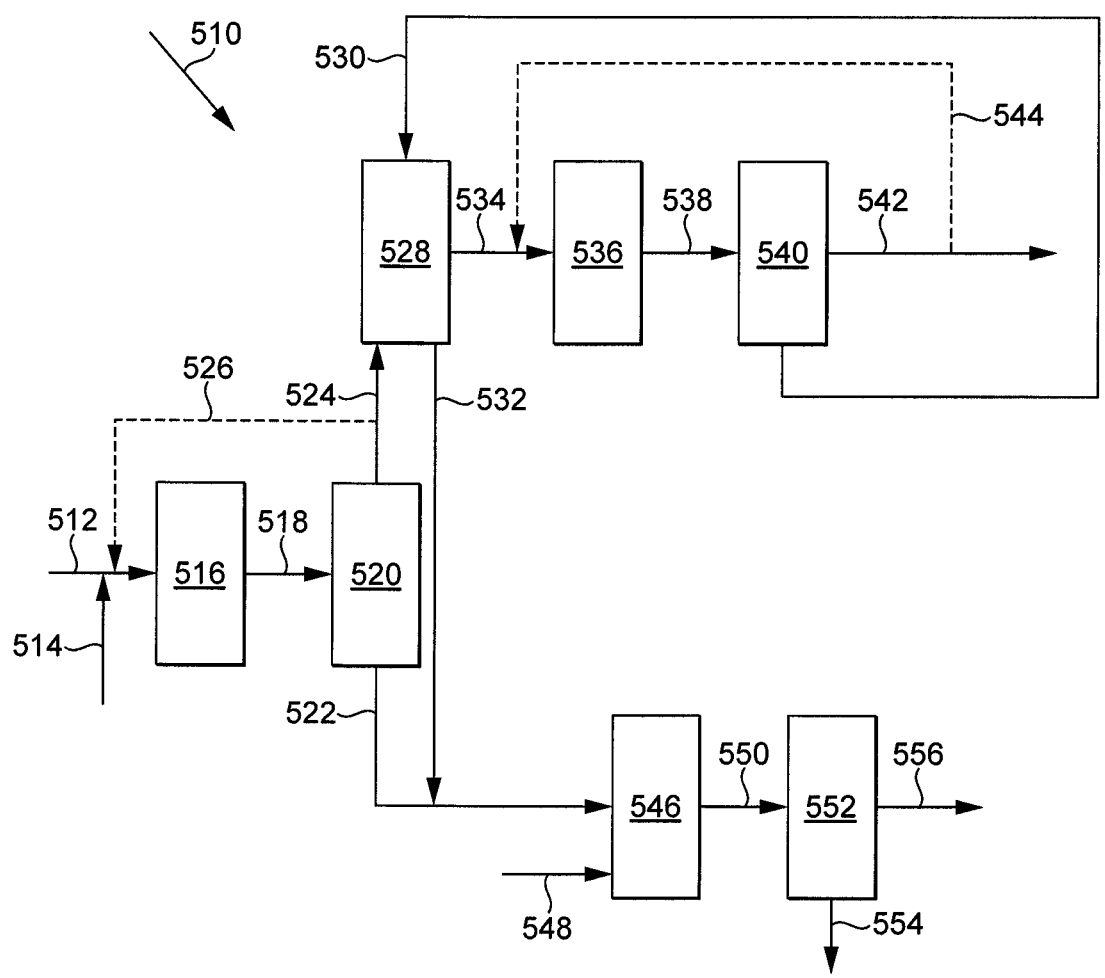
FIG. 5 is a block diagram showing an embodiment of the present invention of an integrated process for the production of acetic acid and incorporating scrubbing of synthesis gas feed for methanol synthesis and supply of a methanol-rich stream to a scrubbing zone.

FIG. 5 is a block diagram showing an embodiment of the present invention of an integrated process for the production of acetic acid and incorporating scrubbing of synthesis gas feed for methanol synthesis and supply of methanol-rich stream to scrubbing zone. The integrated unit 510 includes a synthesis gas feed line 512 and a dimethyl ether feed line 514 connected to a carbonylation reactor 516. In use, a fresh synthesis gas is heated to the desired carbonylation reaction temperature and fed to the carbonylation reactor 516 via the synthesis gas feed line 512. The synthesis gas comprises carbon monoxide, hydrogen and carbon dioxide, and preferably, has a stoichiometric number, in the range 0.9 to 1.3. Dry dimethyl ether is supplied to the carbonylation reactor 516 via the dimethyl ether feed line 514, which joins the synthesis gas feed line 512 before entry to the carbonylation reactor 516. The carbonylation reactor 516 contains a catalyst active for the carbonylation of dimethyl ether to methyl acetate, for example a mordenite zeolite, suitably mordenite in its hydrogen form. The dimethyl ether and synthesis gas are contacted with the catalyst in the carbonylation reactor 516 at a temperature in the range 250° C. to 350° C. and a total pressure in the range 10 to 100 barg (1000 kPa to 10,000 kPa) to form a gaseous carbonylation reaction product comprising methyl acetate and synthesis gas enriched in hydrogen which is withdrawn from the carbonylation reactor 516 via a carbonylation reaction product line 518 and passed to a first separation unit 520 comprising, for example, a heat exchanger and knock-out drum. In separation unit 520, the carbonylation reaction product is cooled, suitably to a temperature in the range 40° C. to 50° C., and a methyl acetate-rich liquid stream and a synthesis gas stream comprising a small amount of methyl acetate, for example an amount in the range 0.1 to 5 mol %, are recovered therefrom. The methyl acetate-rich liquid stream is removed from the separation unit 520 via a methyl acetate liquid line 522. The synthesis gas is removed from the first separation unit 520 via a first synthesis gas line 524 and is optionally divided into a first part and a second part, for example by a suitable valve system, wherein the first part of the synthesis gas, suitably comprising 20 to 30% thereof, is supplied to a scrubbing unit 528 and the second part of the synthesis gas, suitably comprising 70 to 80% thereof, is recycled to the carbonylation reactor 516 via a first synthesis gas recycle line 526. If desired, the synthesis gas recovered from the first separation unit 520 may be passed in its entirety via the first synthesis gas line 524 to the scrubbing unit 528. The scrubbing unit 528 is supplied with a counter-current flow of a liquid scrubbing solvent comprising methanol via a methanol feed line 530, and the synthesis gas comprising methyl acetate passed to the scrubbing unit 528 is contacted therein with the liquid methanol to remove methyl acetate and other components soluble in methanol, suitably dimethyl ether and acetic acid. The methanol containing absorbed methyl acetate is removed from the scrubbing unit 528 via a methanol removal line 532, and the scrubbed synthesis gas depleted in methyl acetate is removed via a scrubbed synthesis gas line 534. The scrubbed synthesis gas is optionally combined with recycle synthesis gas via a second synthesis gas recycle line 544, heated in one or more heat exchangers to the desired methanol synthesis temperature (not shown) and supplied to a methanol synthesis reactor 536. The methanol synthesis reactor 536 contains a catalyst active for the production of methanol, for example a commercial copper-containing methanol synthesis catalyst, for example a Katalco™ catalyst available from Johnson Matthey plc. The scrubbed synthesis gas, optionally combined with recycle synthesis gas, is contacted in the methanol synthesis reactor 536 with the catalyst under methanol synthesis conditions, such as at a temperature in the range 230° C. to 275° C. and at a total pressure in the range 50 to 100 barg (5000 kPa to 10,000 kPa), to generate a methanol synthesis product comprising methanol and unconverted synthesis gas. The methanol synthesis product is withdrawn from the methanol synthesis reactor 536 via a methanol synthesis product line 538, and is supplied to a second separation unit 540 which comprises, for example, a heat exchanger and a knock-out drum, where it is cooled, suitably to a temperature in the range 30° C. to 50° C., and separated to recover a methanol-rich liquid stream and a synthesis gas stream. The methanol-rich liquid stream is recovered from the second separation unit 540 via methanol liquid line 530, and the synthesis gas is recovered from the second separation unit 540 via second synthesis gas line 542 and, if desired, vented in its entirety as a purge gas stream. Optionally, the synthesis gas recovered from the second separation unit 540 may be divided, for example by a suitable valve system, into a first portion suitably comprising 90 to 99% of the synthesis gas, and a second portion suitably comprising 1 to 10% of the synthesis gas, wherein the first portion of the synthesis gas is recycled to the methanol synthesis reactor 536 via a second synthesis gas recycle line 544, which connects to the scrubbed synthesis gas line 534, and the second portion of the synthesis gas is removed as a purge stream. The methanol-rich liquid stream recovered from the second separation unit 540 via the methanol liquid line 530 is recycled to the scrubbing unit 528 for use as the liquid scrubbing solvent. The methyl acetate-rich liquid stream removed from the first separation unit 520 via the methyl-acetate liquid line 522, and the methanol solvent stream containing absorbed methyl acetate removed from the scrubbing unit 528 via methanol removal line 532 are combined, optionally volatilised to the vapour phase, for example in a pre-heater (not shown), and supplied to a dehydration-hydrolysis reactor 546. The dehydration-hydrolysis reactor 546 contains at least one catalyst active for the dehydration of methanol and active for the hydrolysis of methyl acetate, for example a zeolite, such as ferrierite. Water, suitably in an amount of 0.1 to 50 mol % based on the total feed to the dehydration-hydrolysis reactor 546, is supplied to the reactor 546 via a water feed line 548. The methanol and methyl acetate are converted in the dehydration-hydrolysis reactor 546 under dehydration-hydrolysis reaction conditions, suitably at a temperature in the range 100° C. to 350° C. and at atmospheric or greater pressure, to a dehydration-hydrolysis reaction product comprising dimethyl ether and acetic acid, which reaction product is withdrawn from the dehydration-hydrolysis reactor 546 via a dehydration-hydrolysis reaction product line 550. The dehydration-hydrolysis reaction product is supplied to a third separation unit 552 comprising, for example, one or more distillation columns, suitably operated at a temperature in the range 25 C to 200° C. and at a pressure in the range atmospheric to 30 barg (atmospheric to 3000 kPa), to recover an acetic acid-rich stream and a dimethyl ether-rich stream. The acetic acid-rich stream is removed from the third separation unit 552, typically as a bottoms stream, via an acetic acid removal line 554. The dimethyl ether-rich stream is removed from the third separation unit 552, typically as an overhead stream, via a dimethyl ether removal line 556. Both the acetic acid-rich stream and the dimethyl ether-rich stream may also comprise varying amounts of methanol, methyl acetate and water, and these may optionally be removed from the streams and recycled to the dehydration-hydrolysis reactor 546 (not shown).

Figure 6:
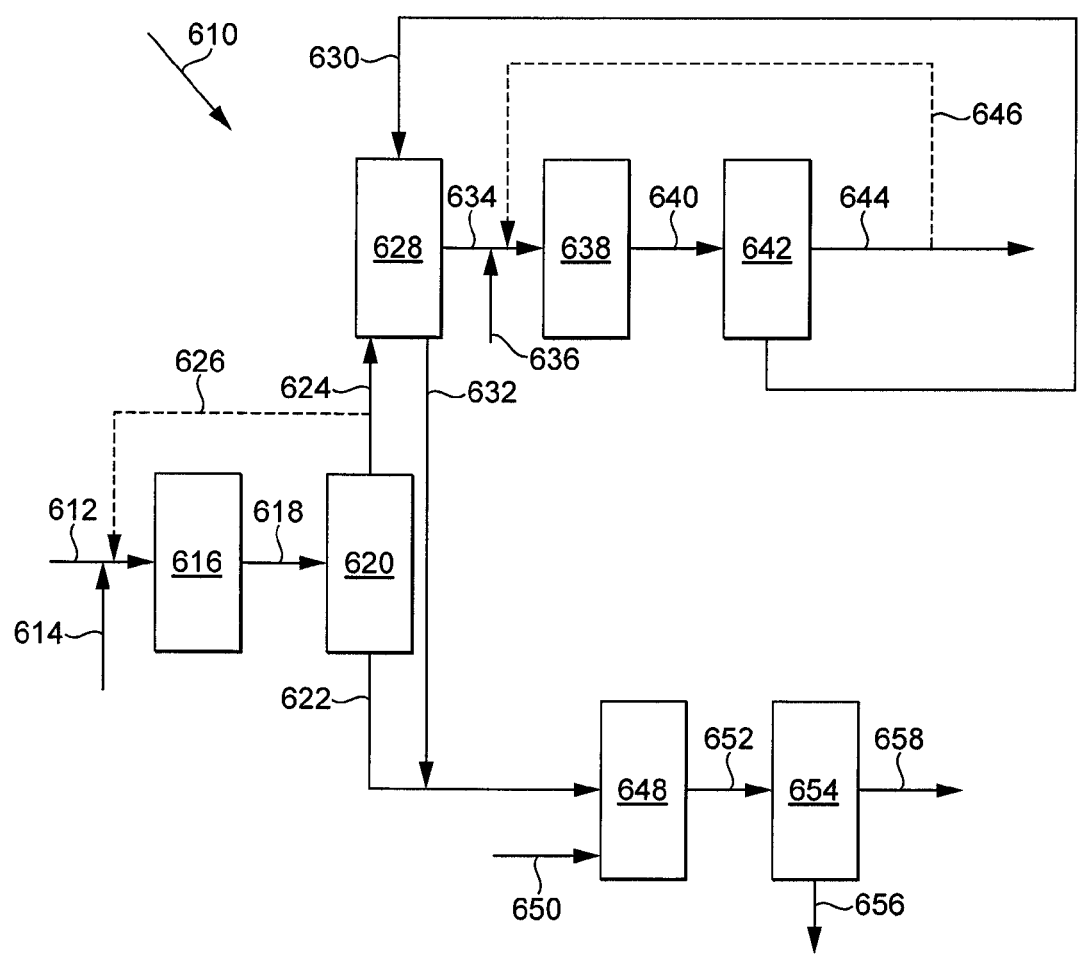
FIG. 6 is a block diagram showing an embodiment of the present invention of an integrated process for the production of acetic acid, incorporating fresh synthesis gas feeds to carbonylation and methanol synthesis and supply of a methanol-rich stream to a scrubbing zone.

FIG. 6 is a block diagram showing an embodiment of the present invention of an integrated process for the production of acetic acid, incorporating fresh synthesis gas feeds to carbonylation and methanol synthesis and supply of a methanol-rich stream to a scrubbing zone. The integrated unit 610 includes a first synthesis gas feed line 612 and a dimethyl ether feed line 614 connected to a carbonylation reactor 616. In use, a first fresh synthesis gas is heated to the desired carbonylation reaction temperature and fed to the carbonylation reactor 616 via the synthesis gas feed line 612. The synthesis gas comprises carbon monoxide, hydrogen and carbon dioxide and, preferably has a stoichiometric number in the range 0.05 to 1.1. Dry dimethyl ether is supplied to the carbonylation reactor 616 via the dimethyl ether feed line 614, which joins the synthesis gas feed line 612 before entry to the carbonylation reactor 616. The carbonylation reactor 616 contains a catalyst active for the carbonylation of dimethyl ether to methyl acetate, for example a mordenite zeolite, suitably mordenite in its hydrogen form. The dimethyl ether and synthesis gas are contacted with the catalyst in the carbonylation reactor 616 at a temperature in the range 250° C. to 350° C. and a total pressure in the range 10 to 100 barg (1000 kPa to 10,000 kPa), to form a gaseous carbonylation reaction product comprising methyl acetate and synthesis gas enriched in hydrogen, which is withdrawn from the carbonylation reactor 616 via a carbonylation reaction product line 618 and passed to a first separation unit 620 comprising, for example, a heat exchanger and knock-out drum. In separation unit 620, the carbonylation reaction product is cooled, suitably to a temperature in the range 40° C. to 50° C., and a methyl acetate-rich liquid stream and a synthesis gas stream comprising a small amount of methyl acetate, for example an amount in the range 0.1 to 5 mol %, are recovered therefrom. The methyl acetate-rich liquid stream is removed from the separation unit 620 via a methyl acetate liquid line 622. The synthesis gas is removed from the first separation unit 620 via a first synthesis gas line 624, and is optionally divided into a first part and a second part, for example by a suitable valve system, wherein the first part of the synthesis gas, suitably comprising 1 to 20 mol % thereof, is supplied to a scrubbing unit 528 and the second part of the synthesis gas, suitably comprising 80 to 99 mol % thereof, is recycled to the carbonylation reactor 616 via a first synthesis gas recycle line 626. If desired, the synthesis gas recovered from the first separation unit 620 may be passed in its entirety via the first synthesis gas line 624 to the scrubbing unit 628. The scrubbing unit 628 is supplied with a counter-current flow of a liquid scrubbing solvent comprising methanol via a methanol feed line 630, and the synthesis gas comprising methyl acetate passed to the scrubbing unit 628 is contacted therein with the liquid methanol to remove methyl acetate and other components soluble in methanol, suitably dimethyl ether and acetic acid. The methanol containing absorbed methyl acetate is removed from the scrubbing unit 628 via a methanol removal line 632, and the scrubbed synthesis gas depleted in methyl acetate is removed via a scrubbed synthesis gas line 634. The scrubbed synthesis gas is combined with a second fresh synthesis gas feed via a second synthesis gas feed line 636, optionally combined with recycle synthesis gas via a second synthesis gas recycle line 646, heated in one or more heat exchangers to the desired methanol synthesis temperature (not shown) and supplied to a methanol synthesis reactor 638. The second fresh synthesis gas comprises carbon monoxide, hydrogen and carbon dioxide. The methanol synthesis reactor 638 contains a catalyst active for the production of methanol, for example a commercial copper-containing methanol synthesis catalyst, for example a Katalco™ catalyst available from Johnson Matthey plc. The scrubbed synthesis gas and fresh synthesis gas feed, optionally combined with recycle synthesis gas, is contacted in the methanol synthesis reactor 638 with the catalyst under methanol synthesis conditions, such as at a temperature in the range 230° C. to 275° C. and at a total pressure in the range 50 to 100 barg (5000 kPa to 10,000 kPa), to generate a methanol synthesis product comprising methanol and unconverted synthesis gas. The methanol synthesis product is withdrawn from the methanol synthesis reactor 638 via a methanol synthesis product line 640, and is supplied to a second separation unit 642 which comprises, for example a heat exchanger and a knock-out drum, where it is cooled, suitably to a temperature in the range 30° C. to 50° C., and separated to recover a methanol-rich liquid stream and a synthesis gas stream. The methanol-rich liquid stream is recovered from the second separation unit 642 via methanol liquid line 630, and the synthesis gas is recovered from the second separation unit 642 via a second synthesis gas line 644 and, if desired, is vented in its entirety as a purge gas stream. Optionally, the synthesis gas recovered from the second separation unit 642 may be divided, for example by a suitable valve system, into a first portion suitably comprising 90 to 99% of the synthesis gas, and a second portion suitably comprising 1 to 10% of the synthesis gas, wherein the first portion of the synthesis gas is recycled to the methanol synthesis reactor 638 via second synthesis gas recycle line 646, which connects to the scrubbed synthesis gas line 634, and the second portion of the synthesis gas is removed as a purge stream. The methanol-rich liquid stream recovered from the second separation unit 642 via the methanol liquid line 630 is recycled to the scrubbing unit 628 for use as the liquid scrubbing solvent. The methyl acetate-rich liquid stream removed from the first separation unit 620 via the methyl-acetate liquid line 622, and the methanol solvent stream containing absorbed methyl acetate removed from the scrubbing unit 628 via methanol removal line 632 are combined, optionally volatilised to the vapour phase, for example in a pre-heater (not shown), and supplied to a dehydration-hydrolysis reactor 648. The dehydration-hydrolysis reactor 648 contains at least one catalyst active for the dehydration of methanol and active for the hydrolysis of methyl acetate, for example a zeolite, such as ferrierite. Water, suitably in an amount of 0.1 to 50 mol % based on the total feed to the dehydration-hydrolysis reactor 648, is supplied to the reactor 648 via a water feed line 650. The methanol and methyl acetate are converted in the dehydration-hydrolysis reactor 648 under dehydration-hydrolysis reaction conditions, suitably at a temperature in the range 100° C. to 350° C. and at atmospheric or greater pressure, to a dehydration-hydrolysis reaction product comprising dimethyl ether and acetic acid, which reaction product is withdrawn from the dehydration-hydrolysis reactor 648 via a dehydration-hydrolysis reaction product line 652. The dehydration-hydrolysis reaction product is supplied to a third separation unit 654 comprising, for example, one or more distillation columns, suitably operated at a temperature in the range 25° C. to 200° C. and at a pressure in the range atmospheric to 30 barg (atmospheric to 3000 kPa), to recover an acetic acid-rich stream and a dimethyl ether-rich stream. The acetic acid-rich stream is removed from the third separation unit 654, typically as a bottoms stream, via an acetic acid removal line 656. The dimethyl ether-rich stream is removed from the third separation unit 654, typically as an overhead stream, via a dimethyl ether removal line 658. Both the acetic acid-rich stream and the dimethyl ether-rich stream may also comprise varying amounts of methanol, methyl acetate and water, and these may optionally be removed from the streams and recycled to the dehydration-hydrolysis reactor 648 (not shown).

Figure 7:
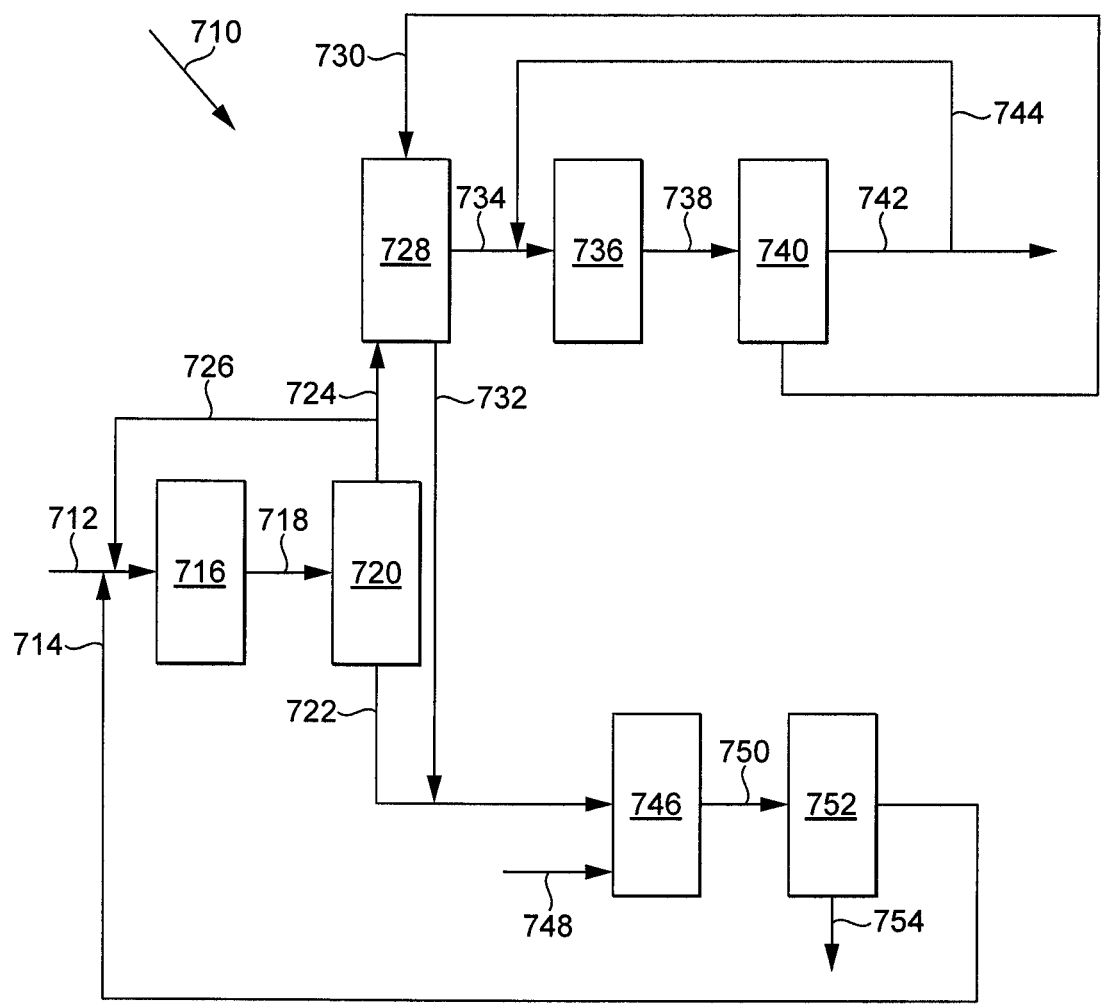
FIG. 7 is a block diagram showing an embodiment of the present invention of an integrated process for the production of acetic acid and incorporating scrubbing of synthesis gas feed for methanol synthesis, supply of a methanol-rich stream to a scrubbing zone and recycle of dimethyl ether to carbonylation.

FIG. 7 is a block diagram showing an embodiment of the present invention of an integrated process for the production of acetic acid and incorporating scrubbing of synthesis gas feed for methanol synthesis, supply of a methanol-rich stream to a scrubbing zone and recycle of dimethyl ether to carbonylation. The integrated unit 710 includes a synthesis gas feed line 712 and a dimethyl ether feed line 714 connected to a carbonylation reactor 716. In use, a fresh synthesis gas is heated to the desired carbonylation reaction temperature and fed to the carbonylation reactor 716 via the synthesis gas feed line 712. The synthesis gas comprises carbon monoxide, hydrogen and carbon dioxide and, preferably, has a stoichiometric number in the range 0.9 to 1.3. Dry, fresh dimethyl ether (not shown) and recycle dimethyl ether is supplied to the carbonylation reactor 716 via the dimethyl ether feed line 714, which joins the synthesis gas feed line 712 before entry to the carbonylation reactor 716. The carbonylation reactor 716 contains a catalyst active for the carbonylation of dimethyl ether to methyl acetate, for example a mordenite zeolite, suitably mordenite in its hydrogen form. The dimethyl ether and synthesis gas are contacted with the catalyst in the carbonylation reactor 716 at a temperature in the range 250° C. to 350° C. and a total pressure in the range 10 to 100 barg (1000 kPa to 10,000 kPa), to form a gaseous carbonylation reaction product comprising methyl acetate and synthesis gas enriched in hydrogen, which is withdrawn from the carbonylation reactor 716 via a carbonylation reaction product line 718 and passed to a first separation unit 720 comprising, for example, a heat exchanger and knock-out drum. In separation unit 720, the carbonylation reaction product is cooled, suitably to a temperature in the range 40° C. to 50° C., and a methyl acetate-rich liquid stream and a synthesis gas stream comprising a small amount of methyl acetate, for example an amount in the range 0.1 to 5 mol %, are recovered therefrom. The methyl acetate-rich liquid stream is removed from the separation unit 720 via a methyl acetate liquid line 722. The synthesis gas is removed from the first separation unit 720 via a first synthesis gas line 724, and is divided into a first part and a second part, for example by a suitable valve system, wherein the first part of the synthesis gas, suitably comprising 20 to 30% thereof, is supplied to a scrubbing unit 728 and the second part of the synthesis gas, suitably comprising 70 to 80% thereof, is recycled to the carbonylation reactor 716 via a first synthesis gas recycle line 726. The scrubbing unit 728 is supplied with a counter-current flow of a liquid scrubbing solvent comprising methanol via a methanol feed line 730, and the synthesis gas comprising methyl acetate passed to the scrubbing unit 728 is contacted therein with the liquid methanol to remove methyl acetate and other components soluble in methanol, suitably dimethyl ether and acetic acid. The methanol containing absorbed methyl acetate is removed from the scrubbing unit 728 via a methanol removal line 732, and the scrubbed synthesis gas depleted in methyl acetate is removed via a scrubbed synthesis gas line 734. The scrubbed synthesis gas is combined with recycle synthesis gas via a second synthesis gas recycle line 744, the combined feed is heated in one or more heat exchangers to the desired methanol synthesis temperature (not shown) and is supplied to a methanol synthesis reactor 736. The methanol synthesis reactor 736 contains a catalyst active for the production of methanol, for example a commercial copper-containing methanol synthesis catalyst, for example a Katalco™ catalyst available from Johnson Matthey plc. The combined synthesis gas is contacted in the methanol synthesis reactor 736 with the catalyst under methanol synthesis conditions, such as at a temperature in the range 230° C. to 275° C. and at a total pressure in the range 50 to 100 barg (5000 kPa to 10,000 kPa), to generate a methanol synthesis product comprising methanol and unconverted synthesis gas. The methanol synthesis product is withdrawn from the methanol synthesis reactor 736 via a methanol synthesis product line 738, and is supplied to a second separation unit 740 which comprises, for example a heat exchanger and a knock-out drum, where it is cooled, suitably to a temperature in the range 30 to 50° C., and separated to recover a methanol-rich liquid stream and a synthesis gas stream. The methanol-rich liquid stream is recovered from the second separation unit 740 via methanol liquid line 730, and the synthesis gas is recovered from the second separation unit 740 via a second synthesis gas line 742. The synthesis gas recovered from the second separation unit 740 is divided, for example by a suitable valve system, into a first portion suitably comprising 90 to 99% of the synthesis gas, and a second portion suitably comprising 1 to 10% of the synthesis gas. The first portion of the synthesis gas is recycled to the methanol synthesis reactor 736 via second synthesis gas recycle line 744, which connects to the scrubbed synthesis gas line 734, and the second portion of the synthesis gas is vented as a purge stream. The methanol-rich liquid stream recovered from the second separation unit 740 via the methanol liquid line 730 is recycled to the scrubbing unit 728 for use as the liquid scrubbing solvent. The methyl acetate-rich liquid stream removed from the first separation unit 720 via the methyl-acetate liquid line 722, and the methanol solvent stream containing absorbed methyl acetate removed from the scrubbing unit 728 via methanol removal line 732 are combined, optionally volatilised to the vapour phase, for example in a pre-heater (not shown), and supplied to a dehydration-hydrolysis reactor 746. The dehydration-hydrolysis reactor 746 contains at least one catalyst active for the dehydration of methanol and active for the hydrolysis of methyl acetate, for example a zeolite, such as ferrierite. Water, suitably in an amount of 0.1 to 50 mol % based on the total feed to the dehydration-hydrolysis reactor 746, is supplied to the reactor 746 via a water feed line 748. The methanol and methyl acetate are converted in the dehydration-hydrolysis reactor 746 under dehydration-hydrolysis reaction conditions, suitably at a temperature in the range 100° C. to 350° C. and at atmospheric or greater pressure, to a dehydration-hydrolysis reaction product comprising dimethyl ether and acetic acid, which reaction product is withdrawn from the dehydration-hydrolysis reactor 746 via a dehydration-hydrolysis reaction product line 750. The dehydration-hydrolysis reaction product is supplied to a third separation unit 752 comprising, for example, one or more distillation columns, suitably operated at a temperature in the range 25° C. to 200° C. and at a pressure in the range atmospheric to 30 barg (atmospheric to 3000 kPa), to recover an acetic acid-rich stream and a dimethyl ether-rich stream. The acetic acid-rich stream is removed from the third separation unit 752, typically as a bottoms stream, via an acetic acid removal line 754. The dimethyl ether-rich stream is removed from the third separation unit 752, typically as an overhead stream, via a dimethyl ether feed line 714 and recycled to the carbonylation reactor 716. Both the acetic acid-rich stream and the dimethyl ether-rich stream may also comprise varying amounts of methanol, methyl acetate and water, and these may optionally be removed from the streams and recycled to the dehydration-hydrolysis reactor 746 (not shown).

Figure 8:
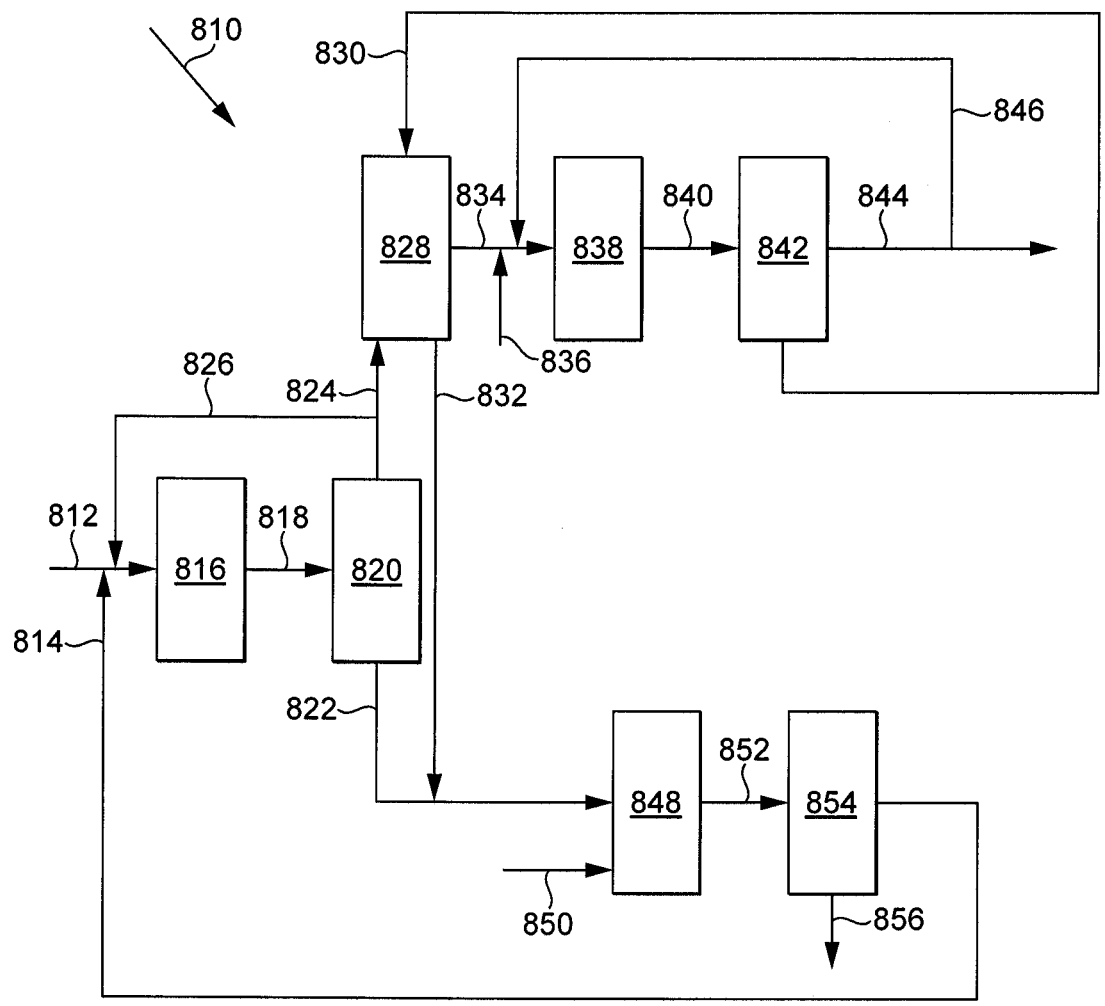
FIG. 8 is a block diagram showing an embodiment of the present invention of an integrated process for the production of acetic acid, incorporating fresh synthesis gas feeds to carbonylation and methanol synthesis, supply of a methanol-rich stream to a scrubbing zone and recycle of dimethyl ether to carbonylation.

FIG. 8 is a block diagram showing an embodiment of the present invention of an integrated process for the production of acetic acid, incorporating fresh synthesis gas feeds to carbonylation and methanol synthesis, supply of a methanol-rich stream to a scrubbing zone and recycle of dimethyl ether to carbonylation. The integrated unit 810 includes a first synthesis gas feed line 812 and a dimethyl ether feed line 814 connected to a carbonylation reactor 816. In use, a first fresh synthesis gas is heated to the desired carbonylation reaction temperature and fed to the carbonylation reactor 816 via the synthesis gas feed line 812. The synthesis gas comprises carbon monoxide, hydrogen and carbon dioxide, and preferably has a stoichiometric number in the range 0.05 to 1.1. Dry fresh dimethyl ether (not shown) and recycle dimethyl ether is supplied to the carbonylation reactor 816 via the dimethyl ether feed line 814, which joins the synthesis gas feed line 812 before entry to the carbonylation reactor 816. The carbonylation reactor 816 contains a catalyst active for the carbonylation of dimethyl ether to methyl acetate, for example a mordenite zeolite, suitably mordenite in its hydrogen form. The dimethyl ether and synthesis gas are contacted with the catalyst in the carbonylation reactor 816 at a temperature in the range 250° C. to 350° C. and a total pressure in the range 10 to 100 barg (1000 kPa to 10,000 kPa), to form a gaseous carbonylation reaction product comprising methyl acetate and synthesis gas enriched in hydrogen, which is withdrawn from the carbonylation reactor 816 via a carbonylation reaction product line 818 and passed to a first separation unit 820 comprising, for example, a heat exchanger and knock-out drum. In separation unit 820, the carbonylation reaction product is cooled, suitably to a temperature in the range 40° C. to 50° C., and a methyl acetate-rich liquid stream and a synthesis gas stream comprising a small amount of methyl acetate, for example an amount in the range 0.1 to 5 mol %, are recovered therefrom. The methyl acetate-rich liquid stream is removed from the separation unit 820 via a methyl acetate liquid line 822. The synthesis gas is removed from the first separation unit 820 via a first synthesis gas line 824, and is divided into a first part and a second part, for example by a suitable valve system, wherein the first part of the synthesis gas, suitably comprising 1 to 20 mol % thereof, is supplied to a scrubbing unit 828 and the second part of the synthesis gas, suitably comprising 80 to 99 mol % thereof, is recycled to the carbonylation reactor 816 via a first synthesis gas recycle line 826. The scrubbing unit 828 is supplied with a counter-current flow of a liquid scrubbing solvent comprising methanol via a methanol feed line 830, and the synthesis gas comprising methyl acetate passed to the scrubbing unit 828 is contacted therein with the liquid methanol to remove methyl acetate and other components soluble in methanol, suitably dimethyl ether and acetic acid. The methanol containing absorbed methyl acetate is removed from the scrubbing unit 828 via a methanol removal line 832, and the scrubbed synthesis gas depleted in methyl acetate is removed via a scrubbed synthesis gas line 834. The scrubbed synthesis gas is combined with a second fresh synthesis gas feed via a second synthesis gas feed line 836 and a recycle synthesis gas via a second synthesis gas recycle line 846, the combined feed is heated in one or more heat exchangers to the desired methanol synthesis temperature (not shown), and supplied to a methanol synthesis reactor 838. The second fresh synthesis gas comprises carbon monoxide, hydrogen and carbon dioxide. The methanol synthesis reactor 838 contains a catalyst active for the production of methanol, for example a commercial copper-containing methanol synthesis catalyst, for example a Katalco™ catalyst available from Johnson Matthey plc. The combined synthesis gas is contacted in the methanol synthesis reactor 838 with the catalyst under methanol synthesis conditions, such as at a temperature in the range 230° C. to 275° C. and at a total pressure in the range 50 to 100 barg (5000 kPa to 10,000 kPa), to generate a methanol synthesis product comprising methanol and unconverted synthesis gas. The methanol synthesis product is withdrawn from the methanol synthesis reactor 838 via a methanol synthesis product line 840, and is supplied to a second separation unit 842 which comprises, for example, a heat exchanger and a knock-out drum, where it is cooled, suitably to a temperature in the range 30° C. to 50° C., and separated to recover a methanol-rich liquid stream and a synthesis gas stream. The methanol-rich liquid stream is recovered from the second separation unit 842 via methanol liquid line 830, and the synthesis gas is recovered from the second separation unit 842 via a second synthesis gas line 844. The synthesis gas recovered from the second separation unit 842 is divided, for example by a suitable valve system, into a first portion suitably comprising 90 to 99% of the synthesis gas, and a second portion suitably comprising 1 to 10% of the synthesis gas. The first portion of the synthesis gas is recycled to the methanol synthesis reactor 838 via second synthesis gas recycle line 846, which connects to the scrubbed synthesis gas line 834, and the second portion of the synthesis gas is vented as a purge stream. The methanol-rich liquid stream recovered from the second separation unit 842 via the methanol liquid line 830 is recycled to the scrubbing unit 828 for use as the liquid scrubbing solvent. The methyl acetate-rich liquid stream removed from the first separation unit 820 via the methyl-acetate liquid line 822, and the methanol solvent stream containing absorbed methyl acetate removed from the scrubbing unit 828 via methanol removal line 832 are combined, optionally volatilised to the vapour phase, for example in a pre-heater (not shown), and supplied to a dehydration-hydrolysis reactor 848. The dehydration-hydrolysis reactor 848 contains at least one catalyst active for the dehydration of methanol and active for the hydrolysis of methyl acetate, for example a zeolite, such as ferrierite. Water, suitably in an amount of 0.1 to 50 mol % based on the total feed to the dehydration-hydrolysis reactor 848, is supplied to the reactor 848 via a water feed line 850. The methanol and methyl acetate are converted in the dehydration-hydrolysis reactor 848 under dehydration-hydrolysis reaction conditions, suitably at a temperature in the range 100° C. to 350° C. and at atmospheric or greater pressure, to a dehydration-hydrolysis reaction product comprising dimethyl ether and acetic acid, which reaction product is withdrawn from the dehydration-hydrolysis reactor 848 via a dehydration-hydrolysis reaction product line 852. The dehydration-hydrolysis reaction product is supplied to a third separation unit 854 comprising, for example, one or more distillation columns, suitably operated at a temperature in the range 25° C. to 200° C. and at a pressure in the range atmospheric to 30 barg (atmospheric to 3000 kPa), to recover an acetic acid-rich stream and a dimethyl ether-rich stream. The acetic acid-rich stream is removed from the third separation unit 854, typically as a bottoms stream, via an acetic acid removal line 856. The dimethyl ether-rich stream is removed from the third separation unit 854, typically as an overhead stream, via a dimethyl ether feed line 814 and recycled to the carbonylation reactor 816. Both the acetic acid-rich stream and the dimethyl ether-rich stream may also comprise varying amounts of methanol, methyl acetate and water, and these may optionally be removed from the streams and recycled to the dehydration-hydrolysis reactor 848 (not shown).

Figure 9:
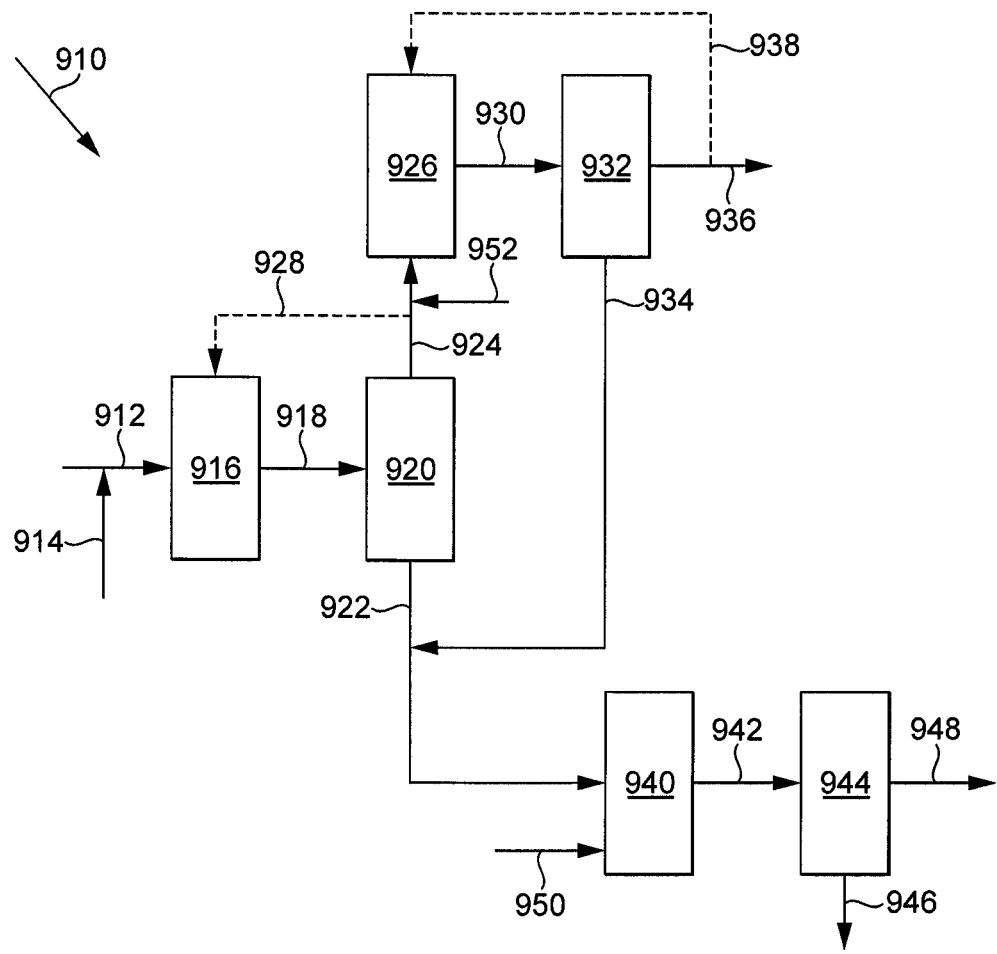
FIG. 9 is a block diagram showing an embodiment of the present invention of an integrated process for the production of acetic acid and incorporating fresh synthesis gas feeds to carbonylation and methanol synthesis.

FIG. 9 is a block diagram showing an embodiment of the present invention of an integrated process for the production of acetic acid and incorporating fresh synthesis gas feeds to carbonylation and methanol synthesis. The integrated unit 910 includes a synthesis gas feed line 912 and a dimethyl ether feed line 914 connected to a carbonylation reactor 916. In use, a first fresh synthesis gas is heated to the desired carbonylation reaction temperature and fed to the carbonylation reactor 916 via the synthesis gas feed line 912. The synthesis gas comprises carbon monoxide, hydrogen and carbon dioxide and, preferably, has a stoichiometric number in the range 0.05 to 1.1. Dry dimethyl ether is supplied to the carbonylation reactor 916 via the dimethyl ether feed line 914, which joins the synthesis gas feed line 912 before entry to the carbonylation reactor 916. The carbonylation reactor 916 contains a catalyst active for the carbonylation of dimethyl ether to methyl acetate, for example a mordenite zeolite, suitably mordenite in its hydrogen form. The dimethyl ether and synthesis gas are contacted with the catalyst in the carbonylation reactor 916 at a temperature in the range 250° C. to 350° C. and a total pressure in the range 10 to 100 barg (1000 kPa to 10,000 kPa), to form a gaseous carbonylation reaction product comprising methyl acetate and synthesis gas enriched in hydrogen, which is withdrawn from the carbonylation reactor 916 via a carbonylation reaction product line 918 and passed to a first separation unit 920 comprising, for example, a heat exchanger and knock-out drum. In separation unit 920, the carbonylation reaction product is cooled, suitably to a temperature in the range 40° C. to 50° C., and a methyl acetate-rich liquid stream and a synthesis gas stream are recovered therefrom. The methyl acetate-rich liquid stream is removed from the separation unit 920 via a methyl acetate liquid line 922. The synthesis gas is removed from the first separation unit 920 via a first synthesis gas line 924. The first synthesis gas line 924 is connected to a methanol synthesis reactor 926. The synthesis gas recovered from the first separation unit 920 is heated in one or heat exchangers (not shown) to the desired methanol synthesis temperature and passed in its entirety to the methanol synthesis reactor 926. If desired, the synthesis gas recovered from the separation unit 920, may be split into two portions, wherein a first portion of the synthesis gas, such as 80 to 99 mol % thereof, optionally compressed to the carbonylation reaction pressure in one or more compressors (not shown), is recycled to the carbonylation reactor 916 via an optional first synthesis gas recycle line 928, and a second portion of the synthesis gas, suitably comprising 1 to 20 mol %, is heated in one or more heat exchangers to the desired methanol synthesis temperature (not shown) and passed to the methanol synthesis reactor 926. A second fresh synthesis gas is combined via a second synthesis gas feed line 952 with the synthesis gas to be passed via synthesis gas line 924 to the methanol synthesis reactor 926. The second fresh synthesis gas comprises carbon monoxide, hydrogen and carbon dioxide. The methanol synthesis reactor 926 contains a catalyst active for the production of methanol, for example a commercial copper-containing methanol synthesis catalyst, for example a Katalco™ catalyst available from Johnson Matthey plc. The synthesis gas passed to the methanol synthesis reactor 926 is contacted with the catalyst therein under methanol synthesis conditions, such as at a temperature in the range 230° C. to 275° C. and at a total pressure in the range 50 to 100 barg (5000 kPa to 10,000 kPa), to generate a methanol synthesis product comprising methanol and unconverted synthesis gas. The methanol synthesis product is withdrawn from the methanol synthesis reactor 926 via a methanol synthesis product line 930, and is supplied to a second separation unit 932 which comprises, for example, a heat exchanger and a knock-out drum, where it is cooled, suitably to a temperature in the range 30° C. to 50° C., and separated to recover a methanol-rich liquid stream and a synthesis gas stream. The methanol-rich liquid stream is recovered from the second separation unit 932 via a methanol liquid line 934, and the synthesis gas is recovered from the second separation unit 932 via a second synthesis gas line 936. The synthesis gas may be, in its entirety, vented as a purge stream, or if desired all or a portion of it, such as 90 to 99% thereof, can be recycled to the methanol synthesis reactor 926 via an optional second synthesis gas recycle line 938. The methyl acetate-rich liquid stream removed from the first separation unit 920 via the methyl-acetate liquid line 922, and the methanol-rich liquid stream removed from the second separation unit 932 via methanol liquid line 934 are combined, optionally volatilised to the vapour phase, for example, in a pre-heater (not shown), and supplied to a dehydration-hydrolysis reactor 940. The dehydration-hydrolysis reactor 940 contains at least one catalyst active for the dehydration of methanol and active for the hydrolysis of methyl acetate, for example a zeolite, such as ferrierite. Water, suitably in an amount of 0.1 to 50 mol % based on the total feed to the dehydration-hydrolysis reactor 940, is supplied to the reactor 940 via a water feed line 950. The methanol and methyl acetate are converted in the dehydration-hydrolysis reactor 940 under dehydration-hydrolysis reaction conditions, suitably at a temperature in the range 100° C. to 350° C. and at atmospheric or greater pressure, to a dehydration-hydrolysis reaction product comprising dimethyl ether and acetic acid, which reaction product is withdrawn from the dehydration-hydrolysis reactor 940 via a dehydration-hydrolysis reaction product line 942. The dehydration-hydrolysis reaction product is supplied to a third separation unit 944 comprising, for example, one or more distillation columns, suitably operated at a temperature in the range 25° C. to 200° C. and at a pressure in the range atmospheric to 30 barg (atmospheric to 3000 kPa), to recover an acetic acid-rich stream and a dimethyl ether-rich stream. The acetic acid-rich stream is removed from the third separation unit 944, typically as a bottoms stream, via an acetic acid removal line 946. The dimethyl ether-rich stream is removed from the third separation unit 944, typically as an overhead stream, via a dimethyl ether removal line 948. Both the acetic acid-rich stream and the dimethyl ether-rich stream may also comprise varying amounts of methanol, methyl acetate and water, and these may optionally be removed from the streams and recycled to the dehydration-hydrolysis reactor 940 (not shown).

Figure 10:
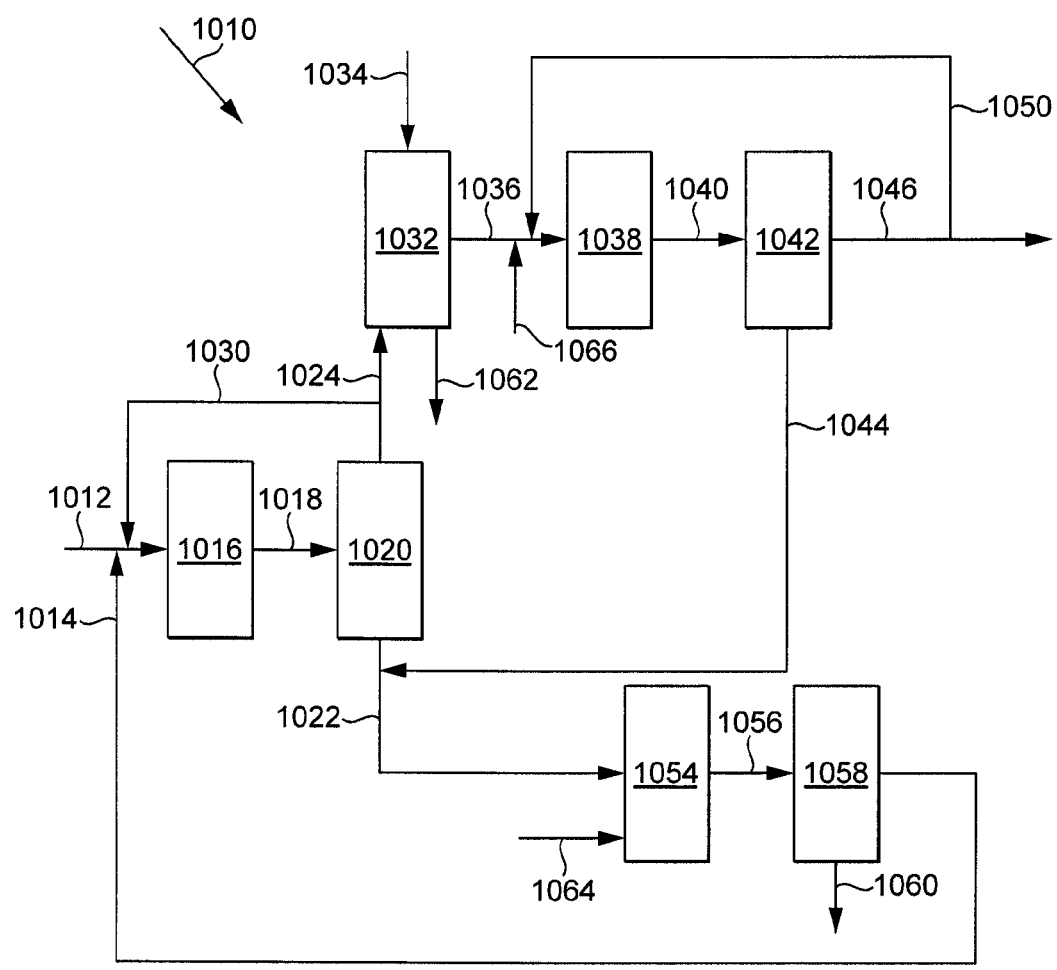
FIG. 10 is a block diagram showing an embodiment of the present invention of an integrated process for the production of acetic acid incorporating fresh synthesis gas feeds to carbonylation and methanol synthesis, scrubbing of synthesis gas for methanol synthesis and recycle of dimethyl ether for carbonylation.

FIG. 10 is a block diagram showing an embodiment of the present invention of an integrated process for the production of acetic acid incorporating fresh synthesis gas feeds to carbonylation and methanol synthesis, scrubbing of synthesis gas for methanol synthesis and recycle of dimethyl ether for carbonylation. The integrated unit 1010 includes a synthesis gas feed line 1012 and a dimethyl ether feed line 1014 connected to a carbonylation reactor 1016. In use, a first fresh synthesis gas is heated to the desired carbonylation reaction temperature and fed to the carbonylation reactor 1016 via the synthesis gas feed line 1012. The synthesis gas comprises carbon monoxide, hydrogen and carbon dioxide and, preferably, has a stoichiometric number in the range 0.05 to 1.1. Dry, fresh dimethyl ether is supplied to the carbonylation reactor 1016 (not shown) and recycle dimethyl ether is supplied to the carbonylation reactor via feed line 1014, which joins the synthesis gas feed line 1012 before entry to the carbonylation reactor 1016. The carbonylation reactor 1016 contains a catalyst active for the carbonylation of dimethyl ether to methyl acetate, for example a mordenite zeolite, suitably mordenite in its hydrogen form. The dimethyl ether and synthesis gas are contacted with the catalyst in the carbonylation reactor 1016 at a temperature in the range 250° C. to 350° C. and a total pressure in the range 10 to 100 barg (1000 kPa to 10,000 kPa), to form a gaseous carbonylation reaction product comprising methyl acetate and synthesis gas enriched in hydrogen, which is withdrawn from the carbonylation reactor 1016 via a carbonylation reaction product line 1018 and passed to a first separation unit 1020 comprising, for example, a heat exchanger and knock-out drum. In separation unit 1020, the carbonylation reaction product is cooled, suitably to a temperature in the range 40 to 50° C., and a methyl acetate-rich liquid stream and a synthesis gas stream comprising a small amount of methyl acetate, for example an amount in the range 0.1 to 5 mol %, are recovered therefrom. The methyl acetate-rich liquid stream is removed from the separation unit 1020 via a methyl acetate liquid line 1022. The synthesis gas is removed from the first separation unit 1020 via a first synthesis gas line 1024, and is divided into a first part and a second part, for example by a suitable valve system. The first part of the synthesis gas, suitably comprising 1 to 20 mol % thereof, is supplied to a scrubbing unit 1032. The second part of the synthesis gas, suitably comprising 80 to 99 mol % thereof, is recycled to the carbonylation reactor 1016 via a first synthesis gas recycle line 1030. The scrubbing unit 1032 is supplied, for example with a counter-current flow of liquid scrubbing solvent, suitably comprising methanol, via a solvent feed line 1034, and the synthesis gas comprising methyl acetate passed to the scrubbing unit 1032 is contacted therein with the liquid scrubbing solvent to remove methyl acetate. The liquid scrubbing solvent containing absorbed methyl acetate and other components soluble in the solvent, suitably dimethyl ether and acetic acid, is removed from the scrubbing unit 1032 via a solvent removal line 1062, and the scrubbed synthesis gas depleted in methyl acetate is removed via a scrubbed synthesis gas line 1036 before being supplied to a methanol synthesis reactor 1038. The methanol synthesis reactor 1038 contains a catalyst active for the production of methanol, for example a commercial copper-containing methanol synthesis catalyst, for example a Katalco™ catalyst available from Johnson Matthey plc. A second fresh synthesis gas is supplied to the methanol synthesis reactor via a second synthesis gas feed line 1066. The second fresh synthesis gas comprises carbon monoxide, hydrogen and carbon dioxide. The second fresh synthesis gas and recycle synthesis gas recovered from the methanol synthesis product are combined with the scrubbed synthesis gas via the synthesis gas feed line 1066 and a second synthesis gas recycle line 1050 respectively. The combined synthesis gas is heated in one or more heat exchangers to the desired methanol synthesis temperature (not shown) and passed to the methanol synthesis reactor 1038, and contacted therein with the catalyst under methanol synthesis conditions, such as at a temperature in the range 230° C. to 275° C. and at a total pressure in the range 50 to 100 barg (5000 kPa to 10,000 kPa), to generate a methanol synthesis product comprising methanol and unconverted synthesis gas. The methanol synthesis product is withdrawn from the methanol synthesis reactor 1038 via a methanol synthesis product line 1040, and is supplied to a second separation unit 1042 which comprises, for example, a heat exchanger and a knock-out drum, where it is cooled, suitably to a temperature in the range 30° C. to 50° C., and separated to recover a methanol-rich liquid stream and a synthesis gas stream. The methanol-rich liquid stream is removed from the second separation unit 1042 via a methanol liquid line 1044, and the synthesis gas is removed from the second separation unit 1042 via a second synthesis gas line 1046. The synthesis gas is divided, for example by a suitable valve system, into a first portion suitably comprising 90 to 99% of the synthesis gas, and a second portion suitably comprising 1 to 10% of the synthesis gas. The first portion of the synthesis gas is recycled to the methanol synthesis reactor 1038 via second synthesis gas recycle line 1050, which connects to the scrubbed synthesis gas line 1036. The second portion of the synthesis gas is removed as a purge stream. The methyl acetate-rich liquid stream removed from the first separation unit 1020 via the methyl-acetate liquid line 1022, and the methanol-rich liquid stream removed from the second separation unit 1042 via methanol liquid line 1044 are combined, optionally volatilised to the vapour phase, for example in a pre-heater (not shown), and supplied to a dehydration-hydrolysis reactor 1054. The dehydration-hydrolysis reactor 1054 contains at least one catalyst active for the dehydration of methanol and active for the hydrolysis of methyl acetate, for example a zeolite, such as ferrierite. Water, suitably in an amount of 0.1 to 50 mol % based on the total feed to the dehydration-hydrolysis reactor 1054, is supplied to the reactor 1054 via a water feed line 1064. The methanol and methyl acetate are converted in the dehydration-hydrolysis reactor 1054 under dehydration-hydrolysis reaction conditions, suitably at a temperature in the range 100 to 350° C. and at atmospheric or greater pressure, to a dehydration-hydrolysis reaction product comprising dimethyl ether and acetic acid, which reaction product is withdrawn from the dehydration-hydrolysis reactor 1054 via a dehydration-hydrolysis reaction product line 1056. The dehydration-hydrolysis reaction product is supplied to a third separation unit 1058 comprising, for example, one or more distillation columns, suitably operated at a temperature in the range 25° C. to 200° C. and at a pressure in the range atmospheric to 30 barg (atmospheric to 3000 kPa), to recover an acetic acid-rich stream and a dimethyl ether-rich stream. The acetic acid-rich stream is removed from the third separation unit 1058, typically as a bottoms stream, via an acetic acid removal line 1060. The dimethyl ether-rich stream is removed from the third separation unit 1058, typically as an overhead stream, via the dimethyl ether feed line 1014 and recycled to the carbonylation reactor 1016. Both the acetic acid-rich stream and the dimethyl ether-rich stream may also comprise varying amounts of methanol, methyl acetate and water, and these may optionally be removed from the streams and recycled to the dehydration-hydrolysis reactor 1054 (not shown).

Figure 11:
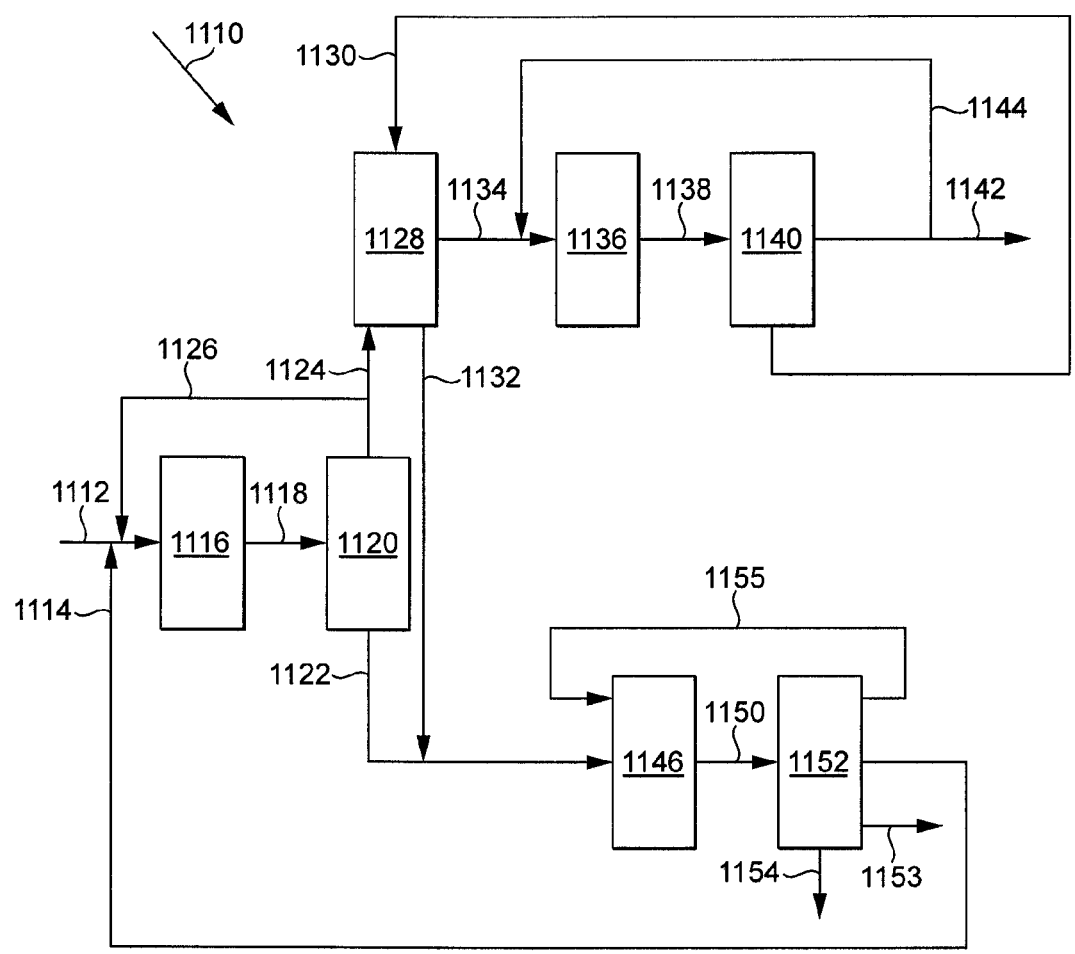
FIG. 11 is a block diagram showing an embodiment of the present invention of an integrated process for the production of acetic acid and incorporating scrubbing of synthesis gas feed for methanol synthesis, supply of a methanol-rich stream to a scrubbing zone and recycle streams to dehydration-hydrolysis and carbonylation.

FIG. 11 is a block diagram showing an embodiment of the present invention of an integrated process for the production of acetic acid and incorporating scrubbing of synthesis gas feed for methanol synthesis, supply of a methanol-rich stream to a scrubbing zone and recycle streams to carbonylation and dehydration-hydrolysis. The integrated unit 1110 includes a synthesis gas feed line 1112 and a dimethyl ether feed line 1114 in connection with a carbonylation reactor 1116. In use, a fresh synthesis gas is heated to the desired carbonylation reaction temperature and fed to the carbonylation reactor 1116 via the synthesis gas feed line 1112. The synthesis gas comprises carbon monoxide, hydrogen and carbon dioxide and, preferably, has a stoichiometric number in the range 0.9 to 1.3. Recycle dimethyl ether is supplied to the carbonylation reactor 1116 via the dimethyl ether feed line 1114, which joins the synthesis gas feed line 1112 before entry to the carbonylation reactor 1116. The carbonylation reactor 1116 contains a catalyst active for the carbonylation of dimethyl ether to methyl acetate, for example a mordenite zeolite, suitably mordenite in its hydrogen form. The dimethyl ether and synthesis gas are contacted with the catalyst in the carbonylation reactor 1116 at a temperature in the range 250° C. to 350° C. and a total pressure in the range 10 to 100 barg (1000 kPa to 10,000 kPa), to form a gaseous carbonylation reaction product comprising methyl acetate and synthesis gas enriched in hydrogen, which is withdrawn from the carbonylation reactor 1116 via a carbonylation reaction product line 1118 and passed to a first separation unit 1120 comprising, for example a heat exchanger and knock-out drum. In separation unit 1120, the carbonylation reaction product is cooled, suitably to a temperature in the range 40° C. to 50° C., and a methyl acetate-rich liquid stream and a synthesis gas stream comprising a small amount of methyl acetate, for example an amount in the range 0.1 to 5 mol %, are recovered therefrom. The methyl acetate-rich liquid stream is removed from the separation unit 1120 via a methyl acetate liquid line 1122. The synthesis gas is removed from the first separation unit 1120 via a first synthesis gas line 1124, and is divided into a first part and a second part, for example by a suitable valve system, wherein the first part of the synthesis gas, suitably comprising 20 to 30% thereof, is supplied to a scrubbing unit 1128 and the second part of the synthesis gas, suitably comprising 70 to 80% thereof, is recycled to the carbonylation reactor 1116 via a first synthesis gas recycle line 1126. The scrubbing unit 1128 is supplied with a counter-current flow of a liquid scrubbing solvent comprising methanol via a methanol feed line 1130, and the synthesis gas comprising methyl acetate passed to the scrubbing unit 1128 is contacted therein with the liquid methanol to remove methyl acetate and other components soluble in methanol, for example dimethyl ether and acetic acid. The methanol containing absorbed methyl acetate is removed from the scrubbing unit 1128 via a methanol removal line 1132, and the scrubbed synthesis gas depleted in methyl acetate is removed via a scrubbed synthesis gas line 1134. The scrubbed synthesis gas is combined with recycle synthesis gas via a second synthesis gas recycle line 1144, the combined feed is heated in one or more heat exchangers to the desired methanol synthesis temperature (not shown) and is supplied to a methanol synthesis reactor 1136. The methanol synthesis reactor 1136 contains a catalyst active for the production of methanol, for example a commercial copper-containing methanol synthesis catalyst, for example a Katalco™ catalyst available from Johnson Matthey plc. The combined synthesis gas is contacted in the methanol synthesis reactor 1136 with the catalyst under methanol synthesis conditions, such as at a temperature in the range 210° C. to 270° C. and at a total pressure in the range 50 to 100 barg (5000 kPa to 10,000 kPa), to generate a methanol synthesis product comprising methanol and unconverted synthesis gas. The methanol synthesis product is withdrawn from the methanol synthesis reactor 1136 via a methanol synthesis product line 1138, and is supplied to a second separation unit 1140 which comprises, for example a heat exchanger and a knock-out drum, where it is cooled, suitably to a temperature in the range 30° C. to 50° C., and separated to recover a methanol-rich liquid stream and a synthesis gas stream. The methanol-rich liquid stream is recovered from the second separation unit 1140 via methanol liquid line 1130, and the synthesis gas is recovered from the second separation unit 1140 via a second synthesis gas line 1142. The synthesis gas recovered from the second separation unit 1140 is divided, for example by a suitable valve system, into a first portion suitably comprising 90 to 99% of the synthesis gas, and a second portion suitably comprising 1 to 10% of the synthesis gas. The first portion of the synthesis gas is recycled to the methanol synthesis reactor 1136 via second synthesis gas recycle line 1144, which connects to the scrubbed synthesis gas line 1134, and the second portion of the synthesis gas is vented as a purge stream 1142. The methanol-rich liquid stream recovered from the second separation unit 1140 via the methanol liquid line 1130 is recycled to the scrubbing unit 1128. The methyl acetate-rich liquid stream removed from the first separation unit 1120 via the methyl acetate liquid line 1122, and the methanol solvent stream containing absorbed methyl acetate removed from the scrubbing unit 1128 via methanol removal line 1132 are combined, optionally volatilised to the vapour phase, for example in a pre-heater (not shown), and supplied to a dehydration-hydrolysis reactor 1146. The dehydration-hydrolysis reactor 1146 contains at least one catalyst active for the dehydration of methanol and active for the hydrolysis of methyl acetate, for example a zeolite, such as ferrierite. Methanol and methyl acetate are converted in the dehydration-hydrolysis reactor 1146 under dehydration-hydrolysis reaction conditions, suitably at a temperature in the range 100° C. to 350° C. and at atmospheric or greater pressure, to a dehydration-hydrolysis reaction product comprising dimethyl ether and acetic acid, which reaction product is withdrawn from the dehydration-hydrolysis reactor 1146 via a dehydration-hydrolysis reaction product line 1150. The dehydration-hydrolysis reaction product is supplied to a third separation unit 1152 comprising, for example one or more distillation columns, suitably operated at a temperature in the range 25° C. to 200° C. and at a pressure in the range atmospheric to 30 barg (atmospheric to 3000 kPa), to recover an acetic acid-rich stream and a dimethyl ether-rich stream. The acetic acid-rich stream is removed from the third separation unit 1152, typically as a bottoms stream, via an acetic acid removal line 1154. The dimethyl ether-rich stream is removed from the third separation unit 1152, typically as an overhead stream, via dimethyl ether feed line 1114 and recycled to the carbonylation reactor 1116. A stream comprising methanol, methyl acetate and water is recovered from the separation unit 1152 and recycled via process line 1155 to the dehydration-hydrolysis reactor 1146. A stream comprising predominantly water is removed as purge stream 1153 from the separation unit 1152.

The invention is now illustrated with reference to the following non-limiting Examples.

EXAMPLE 1

This Example demonstrates the feasibility of an integrated process for the production of acetic acid from dimethyl ether and a synthesis gas comprising carbon monoxide and hydrogen in accordance with the process flow scheme of FIG. 1 except that for the purposes of this Example, a water stream (stream 150) is not fed to the dehydration-hydrolysis reactor 140. In a simulation using ASPEN™ software version 7.3 (Aspen Technology Inc.) a stream of dimethyl ether 114 and a synthesis gas stream 112 consisting of carbon monoxide and hydrogen are supplied to a carbonylation reactor 116 and contacted therein with a mordenite zeolite catalyst under conditions of a temperature of 300° C., a total pressure of 80 bar (8000 kPa) and a total gas hourly space velocity (GHSV) of 3500 h$^{-1}$ to produce a gaseous carbonylation reaction product 118 at a space time yield (STY) of 500 gl$^{-1}$h$^{-1}$ acetic acid equivalent, which reaction product is withdrawn from the carbonylation reactor 116 and passed to a gas/liquid separation unit 120. In separation unit 120 the carbonylation reaction product 118 is cooled to form a liquid product stream rich in methyl acetate 122 and a gaseous synthesis gas stream 124. The synthesis gas stream 124 is heated to 235° C. and passed to the methanol synthesis reactor 126 at a GHSV of 10000 h$^{-1}$ wherein it is contacted with a methanol synthesis catalyst at a total pressure of 75 bar (7500 kPa) to produce a methanol synthesis product 130 at a STY of 950 gl$^{-1}$h$^{-1}$ methanol. The methanol synthesis product 130 is withdrawn from the methanol synthesis reactor 126 and supplied to a separation unit 132 from which a liquid methanol-rich stream 134 and a gaseous synthesis gas stream 136 are recovered. The methanol-rich stream 134 is combined with the methyl acetate-rich product stream 122 and the combined stream is fed to a dehydration-hydrolysis reactor and contacted therein with a zeolite catalyst under conditions of a temperature of 235° C., a total pressure of 14 bar (1400 kPa) and a GHSV of 2000 h$^{-1}$ to produce a reaction product at a STY of 530 gl$^{-1}$h$^{-1}$ acetic acid. A reaction product stream 142 is withdrawn from the dehydration-hydrolysis reactor 140 and separated by distillation in separation unit 144 to obtain an acetic acid-rich product stream 146 and a dimethyl ether-rich product stream 148.

Compositional data for various process streams of FIG. 1 are listed in Table 1 below.

TABLE 1

| | Stream ID | | | | | | | |
|---|---|---|---|---|---|---|---|---|
| moles | 112 | 114 | 122 | 124 | 134 | 136 | 146 | 148 |
| H$_2$ | 2280 | 0 | 6 | 2274 | 0 | 274 | 0 | 6 |
| CO | 2090 | 0 | 6 | 1084 | 0 | 84 | 0 | 6 |

TABLE 1-continued

| | Stream ID | | | | | | | |
|---|---|---|---|---|---|---|---|---|
| moles | 112 | 114 | 122 | 124 | 134 | 136 | 146 | 148 |
| Methanol | 0 | 0 | 0 | 0 | 923 | 77 | 4 | 18 |
| Methyl acetate | 0 | 0 | 960 | 40 | 29 | 11 | 14 | 75 |
| Dimethyl ether | 0 | 1050 | 17 | 33 | 9 | 24 | 46 | 880 |
| Acetic Acid | 0 | 0 | 0 | 0 | 0 | 0 | 873 | 27 |
| Total | 4370 | 1050 | 989 | 3431 | 962 | 470 | 0 | 0 |
| H$_2$:CO | 1.09 | | | 2.10 | | 3.26 | | |
| SN | 1.09 | | | 2.10 | | 3.26 | | |

EXAMPLE 2

This Example demonstrates the feasibility of an integrated process for the production of acetic acid from dimethyl ether and synthesis gas in accordance with the process flow scheme of FIG. 5 except that for the purposes of this Example, a water stream (stream 548) is not fed to the dehydration-hydrolysis reactor 546. In a simulation using ASPEN™ software version 7.3 (Aspen Technology Inc.) a dimethyl ether stream 514 and a synthesis gas stream 512 comprising carbon monoxide, carbon dioxide and hydrogen are supplied as a combined stream to a carbonylation reactor 516 and contacted with a mordenite zeolite catalyst under conditions of a temperature of 300° C., a total pressure of 80 bar (8000 kPa) and a total gas hourly space velocity (GHSV) of 3500 to produce a gaseous carbonylation reaction product stream 518 at a space time yield (STY) of 500 gl$^{-1}$h$^{-1}$ acetic acid equivalent, which reaction product is withdrawn from the carbonylation reactor 516 and passed to a gas/liquid separation unit 520. In separation unit 520 the carbonylation reaction product 518 is cooled to form a liquid product stream rich in methyl acetate 522 and a gaseous synthesis gas stream 524 comprising a small amount of methyl acetate. The synthesis gas stream 524 is passed to a scrubbing unit 528 supplied with a counter-current flow of a liquid methanol stream 530. In scrubbing unit 528 the synthesis gas stream 524 is scrubbed with the liquid methanol stream 530 to provide a synthesis gas stream 534 having a reduced methyl acetate content (scrubbed synthesis gas) and a used methanol stream 532 comprising methanol and absorbed methyl acetate. The scrubbed synthesis gas 534 is removed from the scrubbing unit 528, heated to 235° C. and passed to a methanol synthesis reactor 536 at a GHSV of 10000 h$^{-1}$ wherein it is contacted with a methanol synthesis catalyst at a total pressure of 75 bar (7500 kPa) to produce a methanol synthesis product 538 at a STY of 950 gl$^{-1}$h$^{-1}$ methanol. The methanol synthesis product 538 is withdrawn from the methanol synthesis reactor 536 and supplied to a separation unit 540 from which a liquid methanol-rich stream 530 and a gaseous synthesis gas stream 542 which is vented as a purge stream. The liquid methanol-rich stream 530 is supplied to the scrubbing unit 528. The used methanol stream 532 comprising methanol and absorbed methyl acetate is removed from the scrubbing unit 528 and combined with the liquid methyl acetate-rich stream 522 and the combined stream is fed to a dehydration-hydrolysis reactor 546 and contacted therein with a zeolite catalyst under conditions of a temperature of 235° C., a total pressure of 14 bar (1400 kPa) and a GHSV of 2000 h$^{-1}$ to produce a reaction product at a STY of 530 gl$^{-1}$h$^{-1}$ acetic acid. The reaction product stream 550 is withdrawn from the dehydration-hydrolysis reactor 546 and separated by distillation in separation unit 552 to obtain a acetic acid-rich product stream 554 and a dimethyl ether-rich product stream 556. Compositional data for various process streams of FIG. 5 are listed in Table 2 below

TABLE 2

| moles | Stream ID | | | | | | | | | |
|---|---|---|---|---|---|---|---|---|---|---|
| | 512 | 514 | 522 | 524 | 534 | 530 | 532 | 542 | 554 | 556 |
| $H_2$ | 2576 | 0 | 7 | 2530 | 2524 | 10 | 15 | 395 | 0 | 22 |
| $CH_4$ | 23 | 0 | 1 | 62 | 66 | 6 | 1 | 61 | 0 | 2 |
| $N_2$ | 114 | 0 | 1 | 113 | 115 | 3 | 1 | 113 | 0 | 1 |
| CO | 1938 | 0 | 5 | 933 | 927 | 2 | 8 | 45 | 0 | 13 |
| $H_2O$ | 0 | 0 | 2 | 2 | 2 | 122 | 121 | 0 | 43 | 80 |
| $CO_2$ | 228 | 0 | 19 | 209 | 216 | 28 | 22 | 67 | 0 | 41 |
| Methanol | 0 | 0 | 14 | 2 | 34 | 1030 | 998 | 5 | 21 | 90 |
| Methyl acetate | 0 | 0 | 945 | 39 | 0 | 0 | 39 | 0 | 13 | 71 |
| Dimethyl ether | 0 | 1050 | 10 | 20 | 7 | 6 | 19 | 1 | 46 | 883 |
| Acetic acid | 0 | 0 | 16 | 0 | 0 | 0 | 0 | 0 | 889 | 27 |
| Total | 4879 | 1050 | 1018 | 3911 | 0 | 1206 | 0 | 687 | 1013 | 1230 |
| $H_2$:CO | 1.33 | | | 2.71 | 2.72 | | | 8.75 | | |
| SN | 1.08 | | | 2.03 | 2.02 | | | 2.92 | | |

EXAMPLE 3

Example 2 was repeated except that for the purposes of this Example 3, a water stream (stream 548) was introduced to the dehydration-hydrolysis reactor 546. Compositional data for various process streams of FIG. 5 are listed in Table 3 below.

TABLE 3

| moles | Stream ID | | | | | | | | | |
|---|---|---|---|---|---|---|---|---|---|---|
| | 512 | 514 | 522 | 524 | 534 | 530 | 532 | 542 | 548 | 554 | 556 |
| $H_2$ | 2576 | 0 | 7 | 2530 | 2524 | 10 | 15 | 395 | 0 | 0 | 22 |
| $CH_4$ | 23 | 0 | 1 | 62 | 66 | 6 | 1 | 61 | 0 | 0 | 2 |
| $N_2$ | 114 | 0 | 1 | 113 | 115 | 3 | 1 | 113 | 0 | 0 | 1 |
| CO | 1938 | 0 | 5 | 933 | 927 | 2 | 8 | 45 | 0 | 0 | 13 |
| $H_2O$ | 0 | 0 | 2 | 2 | 2 | 122 | 121 | 0 | 500 | 218 | 405 |
| $CO_2$ | 228 | 0 | 19 | 209 | 216 | 28 | 22 | 67 | 0 | 0 | 41 |
| Methanol | 0 | 0 | 14 | 2 | 34 | 1030 | 998 | 5 | 0 | 21 | 90 |
| Methyl acetate | 0 | 0 | 945 | 39 | 0 | 0 | 39 | 0 | 0 | 13 | 71 |
| Dimethyl ether | 0 | 1050 | 10 | 20 | 7 | 6 | 19 | 1 | 0 | 46 | 883 |
| Acetic acid | 0 | 0 | 16 | 0 | 0 | 0 | 0 | 0 | 0 | 889 | 27 |
| Total | 4879 | 1050 | 1018 | 3911 | 0 | 1206 | 0 | 687 | 500 | 1188 | 1555 |
| $H_2$:CO | 1.33 | | | 2.71 | 2.72 | | | 8.75 | | | |
| SN | 1.08 | | | 2.03 | 2.02 | | | 2.92 | | | |

EXAMPLE 4

This Example demonstrates the feasibility of an integrated process for the production of acetic acid from dimethyl ether and a synthesis gas in accordance with the process flow scheme of FIG. 11. In a simulation using ASPEN™ software version 7.3 (Aspen Technology Inc.) a synthesis gas stream 1112 comprising carbon monoxide, carbon dioxide and hydrogen and a recycle stream of dimethyl ether 1114 are supplied as a combined stream to a carbonylation reactor 1116 and contacted therein with a mordenite zeolite catalyst under conditions of a temperature of 300° C., a total pressure of 80 bar (8000 kPa) and a total gas hourly space velocity (GHSV) of 3500 h$^{-1}$ to produce a gaseous carbonylation reaction product 1118 at a space time yield (STY) of 500 gl$^{-1}$h$^{-1}$ acetic acid equivalent, which reaction product 1118 is withdrawn from the carbonylation reactor 1116 and passed to a gas/liquid separation unit 1120. In separation unit 1120 the carbonylation reaction product 1118 is cooled to form a liquid product stream rich in methyl acetate 1122 and a gaseous synthesis gas stream 1124 comprising a small amount of methyl acetate. The synthesis gas stream 1124 is divided such that a portion of it is recycled as synthesis gas stream 1126 to the carbonylation reactor 1116 and the remainder of the synthesis gas stream 1124 is passed to a scrubbing unit 1128 supplied with a counter-current flow of a liquid methanol stream 1130. In scrubbing unit 1128 the synthesis gas stream 1124 is scrubbed with the liquid methanol stream 1130 to provide a synthesis gas stream 1134 having a reduced methyl acetate content (scrubbed synthesis gas) and a used methanol stream 1132 comprising methanol and absorbed methyl acetate. The scrubbed synthesis gas 1134 is removed from the scrubbing unit 1128, combined with recycle synthesis gas stream 1144, heated to 235° C. and passed to a methanol synthesis reactor 1136 at a GHSV of 10000 h$^{-1}$ wherein it is contacted with a methanol synthesis catalyst at a total pressure of 75 bar (7500 kPa) to produce a methanol synthesis product 1138 at a STY of 950 gl$^{-1}$h$^{-1}$ methanol. The methanol synthesis product 1138 is withdrawn from the methanol synthesis reactor 1136 and supplied to a separation unit 1140 from which a liquid methanol-rich stream 1130 and a gaseous synthesis gas stream are recovered a portion of which is vented as purge stream 1142 and a portion of which is a recycle synthesis gas stream 1144 to the methanol synthesis reactor 1136. The liquid methanol-rich stream 1130 is supplied to the scrubbing unit 1128. The used methanol stream 1132 comprising methanol and absorbed methyl acetate is removed from the scrubbing unit 1128 and combined with the liquid methyl acetate-rich stream 1122 and the combined stream is fed to a dehydration-hydrolysis reactor 1146 and contacted therein with a zeolite catalyst under conditions of a temperature of 235° C., a total pressure of 14 bar (1400 kPa) and a GHSV of 2000 $h^{-1}$ to produce a reaction product at a STY of 530 $gl^{-1}h^{-1}$ acetic acid. A reaction product stream 1150 is withdrawn from the dehydration-hydrolysis reactor 1146 and separated by distillation in separation unit 1152 to obtain an acetic acid-rich product stream 1154, a dimethyl ether-rich product stream 1114, a water-rich stream 1153 and a stream 1155 comprising methanol, methyl acetate and water. Stream 1155 is recycled to the dehydration-hydrolysis reactor 1146 and the dimethyl ether-rich stream 1114 is recycled to the carbonylation reaction unit 1116. Compositional data for various process streams of FIG. 11 are listed in Table 4 below.

ments. The data in Table 5 below clearly demonstrates that the production of methanol from synthesis gas is adversely affected by the presence of methyl acetate.

TABLE 5

| Run No. | Methyl acetate/ mol % | Temp/ ° C. | Time on stream/ hrs | GHSV/ $h^{-1}$ | Sel/% | STY/ g/l · h |
|---|---|---|---|---|---|---|
| 1 | 0 | 260 | 74 | 20000 | 99.9 | 1335 |
| 2 | 1 | 260 | 51 | 20000 | 95.7 | 803 |
| 3 | 0 | 260 | 44 | 20000 | 99.9 | 1041 |
| 4 | 0 | 260 | 74 | 5000 | 99.0 | 407 |
| 5 | 1 | 260 | 51 | 5000 | 96.0 | 364 |
| 6 | 0 | 260 | 44 | 5000 | 99.0 | 409 |

The invention claimed is:

1. An integrated process for the production of acetic acid which process comprises:

TABLE 4

| moles | Stream ID | | | | | | | | | | | | |
|---|---|---|---|---|---|---|---|---|---|---|---|---|---|
| | 1112 | 1114 | 1126 | 1122 | 1124 | 1134 | 1130 | 1132 | 1144 | 1142 | 1155 | 1154 | 1153 |
| $H_2$ | 5424 | 0 | 16517 | 51 | 5332 | 5321 | 27 | 38 | 15743 | 494 | 0 | 0 | 0 |
| $CH_4$ | 100 | 1 | 433 | 4 | 140 | 166 | 30 | 4 | 4323 | 136 | 0 | 0 | 0 |
| $N_2$ | 20 | 0 | 61 | 0 | 20 | 21 | 1 | 0 | 626 | 20 | 0 | 0 | 0 |
| CO | 3982 | 1 | 5686 | 30 | 1836 | 1817 | 2 | 20 | 865 | 27 | 0 | 0 | 0 |
| $H_2O$ | 10 | 1 | 4 | 3 | 1 | 5 | 412 | 408 | 16 | 0 | 4907 | 2 | 474 |
| $CO_2$ | 502 | 114 | 1669 | 78 | 539 | 523 | 56 | 72 | 1887 | 59 | 0 | 0 | 0 |
| Methanol | 0 | 1 | 13 | 24 | 4 | 63 | 2253 | 2194 | 196 | 0 | 1024 | 0 | 4 |
| Methyl acetate | 0 | 0 | 407 | 1744 | 346 | 0 | 0 | 346 | 0 | 0 | 9135 | 0 | 0 |
| Dimethyl ether | 0 | 3067 | 1681 | 386 | 543 | 360 | 326 | 508 | 1090 | 16 | 161 | 0 | 0 |
| Acetic acid | 0 | 0 | 0 | 27 | 0 | 0 | 0 | 0 | 0 | 0 | 110 | 2083 | 1 |
| Total | 10039 | 3185 | 26472 | 2347 | 8760 | 8276 | 3108 | 3591 | 24745 | 752 | 15338 | 2085 | 479 |
| $H_2$:CO | 1.36 | | 2.90 | | 2.90 | 2.93 | | | 18.19 | 18.19 | | | |
| SN | 1.10 | | 2.02 | | 2.02 | 2.05 | | | 5.03 | 5.03 | | | |

EXAMPLE 5

This Example investigates the effect of methyl acetate on methanol synthesis from synthesis gas. Pellets of Katalco™ methanol catalyst (Johnson Matthey plc) were crushed and sieved to a size-fraction of 125-160 microns. A tubular reactor of 9 mm internal diameter was charged with 3 ml of the catalyst diluted 1:1 v/v with quartz chips. The length of the catalyst bed was 100 mm. Synthesis gas of composition 62 mol % $H_2$, 7 mol % CO, 5 mol % $CO_2$, 21 mol % $N_2$ and 5 mol % Ar was fed to the reactor under conditions of a total pressure of 75 bar (7500 kPa) and a temperature of 260° C. and at a total gas hourly space velocity (GHSV) of 5000 $h^{-1}$ (Runs 1 and 3) or at a total gas hourly space velocity GHSV of 20000 $h^{-1}$ (Runs 4 and 6). The experiments were repeated in Runs 2 and 5 using a synthesis gas of composition 62 mol % $H_2$, 7 mol % CO, 5 mol % $CO_2$, 20 mol % $N_2$ and 5 mol % Ar and a co-feed of 1 mol % methyl acetate. In each experiment the exit stream from the reactor was passed to two gas chromatographs (GC's) for analysis of the components of the exit stream. The GC's were a Varian 4900 micro GC with three columns (molecular sieve 5A, Porapak®Q and CP-Wax-52), each column equipped with a thermal conductivity detector and an Interscience trace GC with two columns (CP Sil 5 and CP-Wax-52), each column equipped with a flame ionization detector. Table 5 below provides the space time yields (STY) in grams of methanol product per liter of catalyst per hour and selectivities (Sel) to methanol achieved for each of the experi- (i) feeding synthesis gas and dimethyl ether into a carbonylation reaction zone and reacting therein the synthesis gas and dimethyl ether in the presence of a carbonylation catalyst to form a gaseous carbonylation reaction product comprising methyl acetate and synthesis gas enriched in hydrogen;

(ii) withdrawing carbonylation reaction product from the carbonylation reaction zone and recovering therefrom a methyl acetate-rich liquid stream and a synthesis gas stream;

(iii) passing at least a portion of the synthesis gas recovered from the carbonylation reaction product to a methanol synthesis zone and contacting it therein with a methanol synthesis catalyst to form a methanol synthesis product comprising methanol and unconverted synthesis gas;

(iv) withdrawing methanol synthesis product from the methanol synthesis zone and recovering therefrom a methanol-rich liquid stream and a synthesis gas stream;

(v) supplying at least a portion of the methyl acetate-rich liquid stream and at least a portion of a methanol-rich liquid stream to a dehydration-hydrolysis reaction zone and contacting therein methanol and methyl acetate with at least one catalyst active for the dehydration of methanol and for the hydrolysis of methyl acetate to form a dehydration-hydrolysis reaction product comprising acetic acid and dimethyl ether;

(vi) recovering from the dehydration-hydrolysis reaction product an acetic acid-rich product stream and a dimethyl ether-rich product stream.

2. A process according to claim 1 wherein the synthesis gas recovered from the carbonylation reaction product comprises methyl acetate and wherein at least a portion of the synthesis gas is scrubbed in a scrubbing zone with a liquid scrubbing solvent to generate a scrubbed synthesis gas depleted in methyl acetate and a liquid solvent stream containing absorbed methyl acetate.

3. A process according to claim 2 wherein the synthesis gas recovered from the carbonylation reaction product comprises methyl acetate in an amount in the range 0.1 to 5 mol %.

4. A process according to claim 2 wherein the liquid scrubbing solvent is selected from imported methanol, all or a portion of the methanol-rich stream recovered from the methanol synthesis product and mixtures thereof.

5. A process according to claim 1 which further comprises recycling at least a portion of the synthesis gas stream recovered from the carbonylation reaction product to the carbonylation reaction zone.

6. A process according to claim 5 wherein at least 50 mol % of synthesis gas recovered from the carbonylation reaction product is recycled to the carbonylation reaction zone.

7. A process according to claim 1 wherein the synthesis gas feed (including any recycles) to the carbonylation reaction zone comprises carbon dioxide.

8. A process according to claim 7 wherein the synthesis gas feed comprises carbon dioxide in a total amount in the range 0.5 to 12 mol %.

9. A process according to claim 1 wherein the synthesis gas feed to the carbonylation reaction zone has a stoichiometric number, SN and SN=$(H_2-CO_2)/(CO+CO_2)$, in the range 0.05 to 1.1.

10. A process according to claim 1 wherein the dimethyl ether feed to the carbonylation reaction zone is selected from fresh dimethyl ether, dimethyl ether-rich product stream recovered from the dehydration-hydrolysis reaction product and mixtures thereof.

11. A process according to claim 1 wherein the carbonylation catalyst is an aluminosilicate zeolite which comprises at least one channel which is defined by an 8-member ring.

12. A process according to claim 11 wherein the zeolite has a framework structure type selected from MOR, FER, OFF and GME.

13. A process according to claim 12 wherein the zeolite has a framework structure type MOR and is a mordenite.

14. A process according to claim 1 wherein the synthesis gas and dimethyl ether are reacted in the carbonylation reaction zone under conditions of a temperature in the range 250° C. to 350° C. and a total pressure in the range 50 to 100 barg (5000 kPa to 10,000 kPa).

15. A process according to claim 1 wherein one or more of imported carbon dioxide and water is introduced to the methanol synthesis zone.

16. A process according to claim 1 wherein fresh synthesis gas is supplied to the methanol synthesis zone and the combined stream of fresh synthesis gas and synthesis gas recovered from the carbonylation reaction product passed to the methanol synthesis zone has a stoichiometric number in the range 1.5 to 2.5.

17. A process according to claim 1 which further comprises recycling at least a portion of the synthesis gas stream recovered from the methanol synthesis product to the methanol synthesis zone.

18. A process according to claim 1 wherein the methanol synthesis catalyst comprises copper.

19. A process according to claim 18 wherein the catalyst is based on copper optionally containing zinc, magesium and/or aluminum.

20. A process according to claim 1 wherein synthesis gas is contacted with the methanol synthesis catalyst under conditions of a temperature of from 210° C. to 270° C. and a total pressure in the range 50 to 100 barg (5000 kPa to 10,000 kPa).

21. A process according to claim 1 wherein a portion of the synthesis gas stream recovered from the methanol synthesis product is vented as a purge stream.

22. A process according to claim 1 wherein methanol is recovered from one or more of the methanol synthesis product withdrawn from the methanol synthesis zone, the methanol-rich liquid stream recovered from the methanol synthesis product and liquid solvent streams comprising methanol obtained from scrubbing of synthesis gas recovered from the carbonylation reaction product.

23. A process according to claim 1 wherein the catalyst in the dehydration-hydrolysis reaction zone is selected from one or more of heteropolyacids and salts thereof, polymeric resins and zeolites.

24. A process according to claim 23 wherein the zeolites are selected from ZSM-5, ZSM-35 and ferrierites.

25. A process according to claim 1 wherein methanol and methyl acetate are supplied to the dehydration-hydrolysis reaction zone, including any recycle streams, at a molar ratio in the range 1:1 to 1:10.

26. A process according to claim 1 wherein water is introduced to the dehydration-hydrolysis reaction zone in an amount 0.1 to 50 mol %, based on the total feed of methyl acetate, methanol and water to the reaction zone.

27. A process according to claim 1 wherein methanol and methyl acetate are contacted with the catalyst in the dehydration-hydrolysis zone in the liquid or vapour phase.

28. A process according to claim 1 wherein the dehydration-hydrolysis reaction zone is a reactive distillation column.

29. A process according to claim 1 wherein the acetic acid-rich product stream and the dimethyl ether-rich product stream are recovered from the dehydration-hydrolysis reaction product by distillation.

30. A process according to claim 1 wherein within each of the carbonylation reaction zone, the methanol synthesis zone and the dehydration-hydrolysis reaction zone the reaction is carried out as a heterogeneous vapour phase reaction.

31. A process according to claim 1 wherein the process is operated as a continuous process.

* * * * *